US006380458B1

(12) United States Patent
Lin

(10) Patent No.: US 6,380,458 B1
(45) Date of Patent: Apr. 30, 2002

(54) CELL-LINEAGE SPECIFIC EXPRESSION IN TRANSGENIC ZEBRAFISH

(75) Inventor: Shuo Lin, Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 0 days.

(21) Appl. No.: 08/871,755

(22) Filed: Jun. 9, 1997

(51) Int. Cl.$^7$ .................. A01K 67/027; G01N 33/00; C12N 15/00
(52) U.S. Cl. ................. 800/20; 800/3; 800/25
(58) Field of Search .................. 100/13, 21; 435/320.1, 435/69.1; 800/3, 8, 20, 21, 25

(56) References Cited

FOREIGN PATENT DOCUMENTS

| CA | 2126138 A1 | 12/1995 |
| WO | WO92/16618 | 10/1992 |
| WO | WO96/03034 A1 | 2/1996 |
| WO | WO96/32087 | 10/1996 |

OTHER PUBLICATIONS

J. Joore et al., Mechanisms of Development, "Regulation of the zebrafish goosecoid promoter by mesoderm inducing factors and Xwnt1," Mar. 1996, vol. 55, Iss. 1, pp. 3–18.*
D. Gao et al., Elsevier Science,Structure and transcription of the gene for translation elongation factor 1 subunit alpha of zebrafish (*Danio rerio*), 1997,pp. 1–5.*
Moav et al. Transgenic Research. 2: 153–161, 1993.*
Stuart et al. Development. 109: 577–584, 1990.*
Peters et al. Developmental Biology. 171: 252–257, 1995.*
Michard–Vanhee et al. Immunogenetics. 40: 1–8, 1994.*
Lin et al. Developmental Biology. 161: 77–83, 1994.*
Bayer et al. Development. 115: 421–426, 1992.*
Chen et al. Biotechnology Annual Review. 2: 205–236, 1996.*
Detrich et al. Proc. Natl. Acad. Sci. USA. 92: 10713–10717, Feb. 1995.*
Stuart et al. Development. 103: 403–412, 1988.*
Brewer et al. EMBO Journal. 14(4): 755–766, 1995.*
Palmiter et al. Proc. Natl. Acad. Sci. USA 88: 478–482, Jan. 1991.*
Long et al. Development. 124: 4105–4111, Oct. 1997.*
Al–Adhami, et al., "Ontogenesis of Haematopoietic Sites in *Brachydanio Rerio* (Hamilton–Buchanan) (*Teleostei*)," *Develop. Growth and Differ.* 19(2):171–179 (1977).
Aleström, et al., "Zebrafish, A Vertebrate Model for Transgene Expression and Biological Function" *Animal Biotechnology* 5(2):147–154 (1994).
Allen et al., "Transgene as probes for active chromosomal domains in mouse development," *Nature* 333:852–855 (1988).
Amsterdam, et al., "Requirements for green fluorescent protein detection in transgenic zebrafish embryos" *Gene* 173:99–103 (1996).

Amsterdam, et al., "The *Aequorea victoria* Green Fluorescent Protein Can Be Used as a Reporter in Live Zebrafish Embryos" *Dev. Biology* 171(1):123–129 (1995).
Araki, et al., "A Real Time Analysis System for Gene Expression in Transgenic Fish" *Bull. Natl. Res. Inst. Aquacult.*, Suppl. 2:65–69 (1996).
Bayer, et al., "A transgene containing lacZ is expressed in primary sensory neurons in zebrafish" *Development* 115:421–426 (1992).
Brewer, et al., "Nuclear translocation of a maternal CCAAT factor at the start of gastrulation activates Xenopus GATA–2 transcription," *Embo J* 14(4):757–766 (1995).
Buono, et al., "Transient expression of RSVCAT in transgenic zebrafish made by electroporation" *Mol. Mar. Biol. Biotechnol.* 1(4/5):271–275 (1992).
Chalfie, et al., "Green Fluorescent Protein as a Marker for Gene Expression," *Science* 263:802–805 (1994).
Chang, et al., "Activity of the Distal Positive Element of the Peripherin Gene is Dependent on Proteins Binding to an Ets–like Recognition Site and a Novel Inverted Repeat Site," *J. Biol. Chem.* 271(11):6467–6475 (1996).
Charron, et al., "Multiple Neuron–specific Enhancers in the Gene Coding for the Human Neurofilament Light Chain," *J. Biol. Chem.* 270(51):30604–30610 (1995).
Chen, et al., "Transgenic Fish: Ideal Models for Basic Research and Biotechnological Applications" *Zoological Studies* 34(4):215–234 (1995).
Chen, et al., "Transgenic fish and its application in basic and applied research" *Biotechnology Annual Review* 2:205–236 (1996).
Clark, et al., "Enhancing the efficiency of transgene expression," *Phil. Trans. R. Soc. Lond. B.* 339:226–232 (1993).
Cormack, et al., "FACS–optimized mutants of the green fluorescent protein (GFP)," *Gene* 173(1):33–38 (1996).
Crepieux, et al., "The Ets Family of Proteins: Weak Modulators of Gene Expression in Quest for Transcriptional Partners," *Crit. Rev. Oncog.* 5(6):615–638 (1994).
Culp, et al., "High–frequency germ–line transmission of plasmid DNA sequences injected into fertilized zebrafish eggs" *Proc. Natl. Acad. Sci. USA* 88(18):7953–7957 (1991).
Cumano, et al., "Lymphoid Potential, Probed before Circulation in Mouse, is Restricted to Caudal Intraembryonic Splanchnopleura," *Cell* 86:907–916 (1996).

(List continued on next page.)

Primary Examiner—Deborah Crouch
(74) Attorney, Agent, or Firm—Needle & Rosenberg, P.C.

(57) ABSTRACT

Disclosed are transgenic fish, and a method of making transgenic fish, which express transgenes in stable and predictable tissue- or developmentally-specific patterns. The transgenic fish contain transgene constructs with homologous expression sequences. Also disclosed are methods of using such transgenic fish. Such expression of transgenes allow the study of developmental processes, the relationship of cell lineages, the assessment of the effect of specific genes and compounds on the development or maintenance of specific tissues or cell lineages, and the maintenance of lines of fish bearing mutant genes.

38 Claims, 4 Drawing Sheets

OTHER PUBLICATIONS

"Current Advances in Defining the Zebrafish Genome" Children's Hospital, Boston, MA, Feb. 2–4, 1997 (list of attendees).

Detrich, et al., "Intraembryonic hematopoietic cell migration during vertebrate development," *Proc. Natl. Acad. Sci. USA* 92(23):10713–10717 (1995).

Driever, et al., "A Genetic Screen for Mutations Affecting Embryogenesis in Zebrafish," *Development* 123:37–46 (1996).

Du, et al., "Growth Enhancement in Transgenic Atlantic Salmon by the Use of an "All Fish" Chimeric Growth Hormone Gene Construct" *Bio/Technology* 10:176–181 (1992).

Evans, et al., "The Erythroid–Specific Transcription Factor Eryf1: A New Finger Protein," *Cell* 58:877–885 (1989).

Fann, et al., "Depolarization Differentially Regulates the Effects of Bone Morphogenetic Protein (BMP)–2, BMP–6, and Activin A on Sympathetic Neuronal Phenotype," *J. Neurochem.* 63(6):2074–1079 (1994).

Ghysen, et al., "Cell interactions and gene interactions in peripheral neurogenesis," *Genes & Dev.* 7(5):723–733 (1993).

Gossler, et al., "Mouse Embryonic Stem Cells and Reporter Constructs to Detect Developmentally Regulated Genes," *Science* 244:463–465 (1989).

Groves, et al., "Differential regulation of transcription factor gene expression and phenotypic markers in developing sympathetic neurons," *Development* 121(3):887–901 (1995).

Haffter, et al., "The identification of genes with unique and essential functions in the development of the zebrafish, *Danio rerio,*" *Development* 123:1–36 (1996).

Hanahan, "Transgenic Mice as Probes Into Complex Systems," *Science* 246:1265–1275 (1989).

Hansel, et al., eds., "Genetic Engineering of Animals: Proceedings of the Second Symposium on Genetic Engineering of Animals, held at Cornell University, Ithaca, NY, USA, Jun. 1989", *Journal of Reproduction and Fertility Suppl.* 41:xiv–240 (1990) Table of Contents provided, xiv–vi).

Inoue, et al., "Electroporation as a new technique for producing transgenic fish, " *Cell. Differ. Develop.* 29:123–128 (1990).

Iyengar, et al., "Regulation and expression of transgenes in fish—a review" *Transgenic Res.* 5:147–166 (1996).

Jaenisch, "Transgenic Animals," *Science* 240:1468–1474 (1988).

Jippo, et al., "Abundant Expression of Transcription Factor GATA–2 in Proliferating But Not in Differentiated Mast Cells in Tissues of Mice: Demonstration by In Situ Hybridization," *Blood* 87(3):993–998 (1996).

Johnson, et al., "pXeX, a vector for efficient expression of cloned sequences in Xenopus embryos," *Gene* 147(2):223–226 (1994).

Kavumpurath, et al., "Gene Transfer Methods and Luciferase Gene Expression in Zebra Fish, *Brachydanio Rerio* (Hamilton)" *The Israeli Journal of Aquaculture—Bamidgeh* 45(4):154–163 (1993).

Kelley, et al., "Ventral Expression of GATA–1 and GATA–2 in the Xenopus Embryo Defines Induction of Hematopoietic Mesoderm," *Dev. Biol.* 165(1):193–205 (1994).

Kennedy, et al., "A Common Precursor for Primitive Erythropoiesis and Definitive Haematopoiesis," *Nature* 386:488–493 (1997).

Kimmel, "Genetics and Early Development of Zebrafish," *Trends in Genet.* 5(8):283–288 (1989).

Kothary, et al., "A transgene containing lacZ inserted into the dystonia locus is expressed in neural tube," *Nature* 335:435–437 (1988).

Lawson, et al., "GATA Factors Are Essential for Activity of the Neuron–Specific Enhancer of the Gonadotropin–Releasing Hormone Gene," *Mol. Cell. Biol.* 16(7):3596–3605 (1996).

Lin, et al., "lacZ Expression in Germline: Transgenic Zebrafish Can Be Detected in Living Embryos" *Dev. Biology* 161:77–83 (1994).

Lin, et al., "lacZ Expression in Germline Transgenic Zebrafish Embryos Can Be Detected in Living Embryos" *TIG* 10(4), (1994).

Lin, et al., "Integration of Germ–Line Transmission of a Pseudotyped Retroviral Vector in Zebrafish" *Science* 265:666–669 (1994).

Liu, et al., "Development of Expression Vectors in Transgenic Fish" *Bio/Technology* 8:1268–1272 (1990).

Maeno, et al., "The Role of BMP–4 and GATA–2 in the Induction and Differentiation of Hematopoietic Mesoderm in *Xenopus Laevis,*" *Blood* 88(6):1965–1972 (1996).

Martin, et al., "Transcriptional Activation and DNA Binding by the Erythroid Factor FG–1/NF–E1/Eryf 1," *Genes Dev.* 4(11):1886–1898 (1990).

Medvinsky, et al., "Definitive Hematopoiesis is Autonomously Initiated by the AGM Region," *Cell* 86:897–906 (1996).

Moav, "Developmental and Molecular Genetics in Fish" *Israel J. of Zoology* 40:441–466 (1994).

Moss, et al., "Green fluorescent protein marks skeletal muscle in murine cell lines and zebrafish" *Gene* 173(1):898–98 (1996).

Müller, et al., "Introducing foreign genes into fish eggs with electroporated sperm as a carrier" *Mol. Mar. Biol. Biotechnol.* 1(4/5):276–281 (1992).

Müller, et al., "Efficient Transient Expression System Based on Square Pulse Electroporation and In Vivo Luciferase Assay of Fertilized Fish Eggs," *FEBS Letters* 324(1):27–32 (1993).

Murakami, et al., "Micromachined electroporation system for transgenic fish" *J. Biotechnol.* 34(1):35–42 (1994).

Nakano, et al., "In Vitro Development of Primitive and Definitive Erythrocytes from Different Precursors," *Science* 272:722–724 (1996).

Njølstad, et al., "A zebrafish homologue of the murine Hox–2.1 gene," *FEBS Letters* 230(1,2):25–30 (1988).

O'Kane, et al., "Detection in situ of Genomic Regulatory Elements in Drosophila," *Proc. Natl. Acad. Sci. USA* 84(24):9123–9127 (1987).

Orkin, "Hematopoiesis: How Does it Happen?," *Curr. Opin. Cell. Biol.* 7:870–877 (1995).

Orkin, "GATA–Binding Transcription Factors in Hematopoietic Cells," *Blood* 80(3):575–581 (1992).

Palmiter, et al., "Heterologous Introns Can Enhance Expression of Transgenes in Mice," *Proc. Nat. Acad. Sci. USA* 88(2):478–482 (1991).

Peters, et al., "Rapid Communication: Green Fluorescent Fusion Proteins: Powerful Tools for Monitoring Protein Expression in Live Zebrafish Embryos" *Dev. Biol.* 171(1):252–257 (1995).

Pevny, et al., "Erythroid differentiation in chimaeric mice blocked by a targeted mutation in the gene for transcription factor GATA–1," *Nature* 349:257–260 (1991).

Powers, et al., "Electroporation: a method for transferring genes into the gametes of zebrafish (*Brachydanio rerio*), channel catfish (*Ictalurus punctatus*), a common carp (*Cyprinus carpio*)" *Mol. Mar. Biol. Biotechnol.* 1(4/5):301–308 (1992).

Ramain, et al., "pannier, a negative regulator of achaete and scute in Drosophila, encodes a zinc finger protein with homology to the vertebrate transcription factor GATA–1," *Development* 119(4):1277–1291 (1993).

Ransom, et al., "Characterization of Zebrafish Mutants with Defects in Embryonic Hematopoiesis," *Development* 123:311–319 (1996).

Reinhard, et al., "Neural selective activation and temporal regulation of a mammalian GAP–43 promoter in zebrafish," *Development* 120(7):1767–1775 (1994).

Roush, "A Zebrafish Genome Project?" *Science* 275:923 (1997).

Streisinger, "Attainment of Minimal Biological Variability and Measurements of Genotoxicity: Production of Homozygous Diploid Zebra Fish," *Natl. Cancer Inst. Monogr.* 65:53–58 (1984).

Stuart, et al., "Replication, integration and stable germ–like transmission of foreign sequences injected into early zebrafish embryos" *Development* 103:403–412 (1988).

Stuart, et al., "Stable lines of transgenic zebrafish exhibit reproducible patterns of transgene expression" *Development* 109:577–584 (1990).

Sun, et al., "ES–like cell cultures derived from early zebrafish embryos" *Mol. Mar. Biol. Biotechnol.* 4(3):193–199 (1995).

Symonds, et al., "Electroporation of salmon sperm with plasmid DNA: evidence of enhanced sperm/DNA association," *Aquaculture* 119:313–327 (1994).

Szelei, et al., "Liposome–mediated gene transfer in fish embryos," *Transgenic Res.* 3:116–119 (1994).

Tsai, et al., "An early haematopoietic defect in mice lacking the transcription factor GATA–2," *Nature* 371:221–226 (1994).

Tsai, et al., "Cloning of cDNA for the major DNA–binding protein of the erythroid lineage through expression in mammalian cells," *Nature* 339:446–451 (1989).

Walmsley, et al., "Negative control of Xenopus GATA–2 by activin and noggin with eventual expression in precursors of the ventral blood islands," *Development* 120(9):2519–2529 (1994).

Weinstein, et al., "Hematopoietic Mutations in the Zebrafish," *Development* 123:303–309 (1996).

Weiss, et al., "GATA transcription factors: Key regulators of hematopoiesis," *Exp. Hematol.* 23(2):99–107 (1995).

Westerfield, et al., "Specific activation of mammalian Hox promoters in mosaic transgenic zebrafish" *Genes & Development* 6:591–598 (1992).

Yamamoto, et al., "Activity and Tissue–Specific Expression of the Transcription Factor NF–E1 Multigene Family," *Genes & Development* 4(10):1650–1662 (1990).

Zelenin, et al., "The Delivery of Foreign Genes Into Fertilized Fish Eggs Using High–velocity Microprojectiles," *FEBS Letters* 287(1 and 2): 118–120 (1991).

Zhao, et al., "Application of Baekonization: a new approach to produce transgenic fish" *Mol. Mar. Biol. Biotechnol.* 2(1):63–69 (1993).

Zolotukhin, et al., "A 'Humanized' Green Fluorescent Protein cDNA Adapted for High–Level Expression in Mammalian Cells," *J. Virol.* 70(7):4646–4654 (1996).

Zon, "Developmental Biology of Hematopoiesis," *Blood* 86(8):2876–2891 (1995).

Zon, et al., "Expression of GATA–binding proteins during embryonic development in *Xenopus laevis*," *Proc. Natl. Acad. Sci. USA* 88(23):19642–19646 (1991).

Culp et al. Proc. Natl Academy Sci. USA. 88: 7953–7957, Sep. 1991.*

Meng, et al., "Promoter analysis in living zebrafish embryos identifies a cis–acting motif required for neuronal expression of GATA–2." *Proc. Natl. Acad. Sci. USA* 94:6267–6272 (1997).

* cited by examiner

IVS-1
AGACACAGTCCAG(GTGAGTCCAA.....1.6 kb.....ATTAAAACAG)TTCGCCAAGTC
 R  H  S  P                                           V  R  Q  V

IVS-2
CTTTCGCCCACCTG(GTATGTTGTG.....0.07kb.....AATTTTACAG)AGGCTCGTGAA
 L  S  P  P                                          E  A  R  E

IVS-3
AAAAAGAGGCTG(GTATGTAAAA.....1.7 kb.....CCTGCATCAG)ATTGTCAGCAAA
 K  K  R  L                                        I  V  S  K

IVS-4
AAACTGCACAAT(GTGAGTATAC.....0.08kb.....CTTTTTGCAG)GTCAACAGGCCT
 K  L  H  N                                         V  N  R  P

FIG. 4

```
NEURON
ENHANCER          GM2
[====]---[/////////////]  nsP5-GM2
[======]---[/////////////]  nsP6-GM2
[======]▪[/////////////]  ns-XS-GM2
        ▪[/////////////]  Xs-GM2
```

FIG. 5

Bar chart: % of embryos expressing GFP in neurons

- nsP5-GM2 (296): ~72
- ns-Xs-GM2 (130): ~8
- Xs-GM2 (210): ~0
- nsP6-GM2 (81): ~7

SEQUENCE LISTING

```
<160> NUMBER OF SEQ ID NOS: 27

<210> SEQ ID NO 1
<211> LENGTH: 26
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 1
ccggatcctg caagtgtagt attgaa                                           26

<210> SEQ ID NO 2
<211> LENGTH: 21
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 2
```

```
aatgtatcaa tcatggcaga c                                              21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 3
tgtatagttc atccatgcca tgtg                                           24

<210> SEQ ID NO 4
<211> LENGTH: 21
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 4
atgaaccttt ctactcaagc t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 5
gctgcttcca cttccactca t                                              21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 6
agacacagtc caggtgagtc caa                                            23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 7
ctttcgccac ctggtatgtt gtg                                            23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 8
aaaaagaggc tggtatgtaa aa                                             22
```

<210> SEQ ID NO 9
<211> LENGTH: 22
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 9
aaactgcaca atgtgagtat ac                                              22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 10
attaaaacag ttcgccaagt c                                               21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 11
aattttacag aggctcgtga a                                               21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 12
cctgcatcag attgtcagca aa                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 13 cttttttgcag gtcaacaggc ct                                             22

<210> SEQ ID NO 14
<211> LENGTH: 8
<212> TYPE: PRT
<213> ORGANISM: Artificial Sequence
<220> FEATURE:
<223> OTHER INFORMATION: Description of Artificial  Sequence; Note =
      Synthetic Construct

<400> SEQUENCE: 14

Arg His Ser Pro Val Arg Gln Val
 1               5

```
<210> SEQ ID NO 15
<211> LENGTH: 8
<212> TYPE: PRT
<213> ORGANISM: Artificial Sequence
<220> FEATURE:
<223> OTHER INFORMATION: Description of Artificial  Sequence; Note =
      Synthetic Construct

<400> SEQUENCE: 15

Leu Ser Pro Pro Glu Ala Arg Glu
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial  Sequence; Note =
      Synthetic Construct

<400> SEQUENCE: 16

Lys Lys Arg Leu Ile Val Ser Lys
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial  Sequence; Note =
      Synthetic Construct

<400> SEQUENCE: 17

Lys Leu His Asn Val Asn Arg Pro
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial  Sequence; Note =
      Synthetic Construct

<400> SEQUENCE: 18

Trp Gly Ala Thr Ala Arg
 1               5

<210> SEQ ID NO 19
<211> LENGTH: 28
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 19
atggatcctc aagtgtccgc gcttagaa                                         28

<210> SEQ ID NO 20
<211> LENGTH: 33
<212> TYPE: DNA
<213> ORGANISM: Artificial Sequence
<220> FEATURE:
<223> OTHER INFORMATION: Description of Artificial  Sequence; Note =
      Synthetic Construct
```

<400> SEQUENCE: 20
tctgcgccgc tttctgcccc ctcctgccct ctt          33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 21
tctgcgaagc tttctgcccc ctcctgccct ctt          33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 22
tctgcgccgc tttctgaacc ctcctgccct ctt          33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 23
tctgcgccgc tttctgccaa ctcctgccct ctt          33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 24
tctgcgccgc tttctgcccc aaactgccct ctt          33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial  Sequence; Note =
      Synthetic Construct

<400> SEQUENCE: 25
tctgcgccgc tttctgcccc ctcctgccct ctt          33

<210> SEQ ID NO 26
<211> LENGTH: 5563
<212> TYPE: DNA
<213> ORGANISM: Artificial Sequence
<220> FEATURE:
<223> OTHER INFORMATION: Description of Artificial  Sequence; Note =
      Synthetic Construct
<221> NAME/KEY: misc_feature
<222> LOCATION: (1)...(5563)

<223> OTHER INFORMATION: N = A,T, C, or G

<400> SEQUENCE: 26

| | | | | | |
|---|---|---|---|---|---|
| gaattctagt | tctagggtaa | actatacagt | tttttttaatt | aataaagttg g | tggaggtaa | 60 |
| atgtctttaa | tgagtaagtc | actgaatcat | ttattcattt | gatttgttca a | acagttgat | 120 |
| tcatttagaa | attcattaga | atcaarctg | cagtctttat | gaacgacccg t | taaaccttt | 180 |
| agtttatgtg | attggaatca | aaccccact | gtgtgttaat | cagatgaatg c | tgaaaagca | 240 |
| cagacaggtt | ttaatccatc | atgccattcc | ttctagaaag | gaaacattag t | aatggtttt | 300 |
| aattttcagc | attttaataa | ccacaagcac | atttctaatg | caatgaaatc a | tatttgcaa | 360 |
| accaaaacag | ctgattcttg | aaatggccta | cacagagtcc | agacctgaat a | ttatagaga | 420 |
| tggtgcagta | tcacttgaaa | gaaaaataaa | cattaatctt | aaatctaaag a | acttaaatc | 480 |
| taaagaagca | ctatgagaaa | tgctgaaaaa | gcctgatttt | acatagcaca t | tatttaaaa | 540 |
| tgaaacctca | gggacagtat | acagaacagt | tcaaatacag | tatacagtaa a | cagaacagg | 600 |
| tcaggtcaca | ccaaatactg | gcaagccatt | ttattctgaa | aatgtttcat t | tagattaga | 660 |
| acagaagaac | tanagagacc | nnnaaagttg | gctgaatata | aataaatata c | cactgcttt | 720 |
| gacggytcta | gacttttgca | cagtacttaa | atgcagtact | taaagtaatt c | ntcatttag | 780 |
| atgagctaag | taaactatga | gttgtgaaaa | acacaccat | tgtgtgatga g | cagtgaggg | 840 |
| tgtcactgta | gctgtgaatt | tgttcatgta | gtgccattac | tagttatacg a | tccccaacc | 900 |
| tcccactcca | atntagatag | cttcttatca | cagttcagca | gcagcgcaca c | acacagaaa | 960 |
| cacacacaca | gccacatccn | tcaaaantgg | tctttggaga | cttctttctc t | ttgaccgtt | 1020 |
| tagttttcgt | gagcataatt | aagttactct | atacaataaa | atgtgagtaa a | tggacacca | 1080 |
| tagatgtcta | aataaataaa | cacataaata | aaaagatgac | actttcacat a | acaccatca | 1140 |
| aacagcttca | taaaattata | ttatatagaa | tattctataa | ttatgttgat t | tgtaacgca | 1200 |
| ctgtaaaaaa | aggattactg | ccttaaattg | ataatttgtt | gaagaaaatt t | actttcctg | 1260 |
| aacatttatt | gtattaatat | attacagtac | gctcaataat | acatgtgaaa c | tgcagcttc | 1320 |
| atatttttaa | atgttttaat | gtatttaata | tatatatata | taatatttat a | tatatatgt | 1380 |
| atgcatgtat | gcatatttat | tctgttgaaa | ggagattagt | tttattcaac a | cattagttt | 1440 |
| taataactcg | tttctaataa | ctgatttctt | ttatctttgt | catgatgaca g | taaataata | 1500 |
| tttgactaga | tatttttcaa | gacatttcta | taccacttaa | agtgacattt a | aaggcttaa | 1560 |
| ctaggttaat | taggttaagt | aagcaggtta | gggtaattgg | gtaagttatt g | tacaacaat | 1620 |
| ggtttgttct | gtagactatt | gaaaaaaatg | gcttaaaggg | gctaataatt t | tgtcccta | 1680 |
| aaatggtgtt | taaaaatgta | aactgctttt | attgtggctg | aaaaaacaaa t | aagaatttc | 1740 |
| tccagaaaaa | aaaatattat | cagacactgt | gaaaatgtcc | ttactctgtt a | aacataatt | 1800 |
| tgtgaaatat | gtaaaaaga | ataaaaaatt | cacatggggg | gtgataactt c | aactacaca | 1860 |
| cacacacaca | cacacacaca | cacatttcag | tgaccaaaat | atgttgtrgg t | ttntktntt | 1920 |
| cattgatata | aaatgtgcga | tgccatttcm | aaaatccata | tatagtttat g | caacattat | 1980 |
| attggamcca | aaataagtaa | tatacaaaat | aagtagtatt | atcttatcca g | tatatttga | 2040 |
| gtatttatat | atcgaagttt | agattcytaa | tttaacaata | tttatgaatt a | tatgtttaa | 2100 |
| gttctaaaac | aacacctcat | gtaaatcaat | aacatggtgc | ttggtacagt a | tgctcaata | 2160 |
| atacatgaaa | aactgcagct | tcatatttaa | aaatgttatt | gtatgcaatt a | catgtacaa | 2220 |
| ttacaaaataa | cgtatggtaa | tgtatacaaa | tatatattta | gtaatagagg g | tataatata | 2280 |

```
tgtgatgcac atgcgaaaaa atatatcaca cacacacgca cgcacgcaca c acacacaca    2340 cacacacatt tatttatgca tatgtacact ataaaaccca aaaagttaaa c tcaaaccat    2400 ttaaggaaac tgattgcaac aaaccattaa agttgaaaaa cgaatcctaa t gagtactgt    2460 aaactgaatn tatttgagta acgaagcaa tttgaggaca gtaaaaccca a taaatgaag    2520 agaactcaaa ccaactgagc actgtaaaac ctaacaagtt aaggcaactc a aaccgtttg    2580 aggaaatcga taagagtc ctgtgaactg tatttaatta actcattact t caaaactct    2640 tttcaaatta gtagaattaa cattcagtac attttgagtt actacactca t ttcatttga    2700 taaagttgac tgttgggttt tacagtgtat ctttttatta atttatataa g aacatgtgt    2760 ggataatata agtacattta ttaacatcat tatatatgtg gcttcagctt t atgcaaatg    2820 ctgaaagtta acgaattgaa atcaattaag catttcagta acataacacg t attgtaggt    2880 tttgtcttca ttgatataca catgcaatgc atttcaagtc atttataatt g atgcattat    2940 attgtattgt accaatgtaa gtaatatata atactata ttatattatc c agtatattt    3000 gactttaaaa tattaaagtt tagattccta atgtaacaat acatatataa t atgttaagg    3060 ttctagaatg gaaccttatg taaatcaawa acctggcgct tggtgaagga t ttgcttctc    3120 tgratctcat cccagtttcc ctgaaaatta taaatgcaca atggtggarg g aagttgaaa    3180 gtgttttgcc tgtcaaatga rartgacagt cttagtcctg tgctccggca g sccgttctg    3240 cgtccgtatc tctcaccatg attgcagcat tkgagtttat ttgcattact g ttctttgct    3300 gagctgcacc aggggaaaag tgcttttgca ttttcattcg ctttgttcac a gtcaccgtt    3360 tccatcccaa gtgctctttg ttaacactt tgcacgccatt ttaattgcca a atgtattag    3420 gccacagcat atgcttaatt cttttcaaca atgaaacttt attaatgatg t gcttgaatc    3480 atagatacta taagttatg gttgttgtaa aattargttt ctctggctgt c tgtgggatt    3540 ttcccagcgc tgttggattt gcgtctttat ctatatttat aagtgaagcc a ttttatata    3600 atctctgaca gtattttatt tagattagaa attaaatact agtgtttttt g tcttgtttc    3660 tatagtatta ttactatttt tttgcattaa tttacagaag atgcctgata a actgaattt    3720 agtataataa tttaaatacc aaaacatcat taggtacatt taaaatacca a tcatgcaaa    3780 aaaataaccc tttgactgca catttaccca atgggtgtcc atttttgact t tttaaataa    3840 tggtttacac acacatcatt gctggtttac aaaaaaatca aacataattc t tttgcacga    3900 ctactctgaa ttttggtttc attcatttc tttttggcta agtctgttta t taatatgga    3960 gtcgccacag cggaatgaat cgccaactta tttagcatat gtttcacaca g tggatgccc    4020 ttccagctgc aaaccatcac tgggaaacat ccatacacta tgggacaatt t agcctaccc    4080 aattcatctg aactgcatgt ctttgcaggg aaacccacac aaacacgggg g agaacatgt    4140 ttggtttaat tgtaaaaaaa caaccagaaa gcataataaa tgagaatctc a atatttttt    4200 accgcatact tcaaaaataa agatgattta gtattaaaaa atgttttatt t gaatattg    4260 cttttaaata aattggsctt acacttagta tatgtattaa ttccagtact t ttaccataa    4320 accgacatat cmaccatttg gtagaggttg atattttaga aatgacgara w tgtgttgaaa    4380 aaaatgcatc gagtgtgtag caacattagg arttaagtat tgcaatgcaa a aattgtaag    4440 twaatcaatt agggactaat tawtcgtcaa tttaaattgt tataatttgc t actttttct    4500 caaaccacta ggtttcactg attattcagc aaaatgttat tcatcatttt c aatttttata    4560 tattttaaca tgagcagcat ttttacttta atatatactg cacaaaaaat a gttacattg    4620
```

-continued

```
tgtttttaag cgtttcctttt attatttat ttttttgagc agtatatttt t aaaaagtga    4680 gaataaatat gtagctttag ttttacataa ccatatgatg cacttaacga t gatgaaaca    4740 tttcattcat atttggggca ttttattttt acttattttt tttgaaaaaa t ggacactaa    4800 ctgtggtttt aatatgattt ctatgtaaat aaaatgactt ttggacattt a atttgatgt    4860 acactgtaaa aaaatccaa ccttaaattt taagttaaat caagttaacc t tatcagtac    4920 attgaactta aattatgtta aactgacata aaactgaatg aataacttat a aaattaagt    4980 tagaacacca tagattaatg ttacaatgaa ctaaaaactg tcatgactaa t tgttcatat    5040 ttatattttt acagtgtaga tgtggaacat ccagtctttg tytataaggt c atataggct    5100 aaaatytaat aaaacattta aataggaatt aaaattttg tttcttaata t ttttattgt    5160 aatttcctaa catttactca gtgaaactaa tttcagtttt gattctttca c tataatatg    5220 tgtatatatg tgtattataa aaataatttg tgttcaaaat aaaataaaaa a atttgcaca    5280 atcctccact attcatttga actgaactca catgctgtgt cagctagaga t ctgccatat    5340 aatattcaaa atggaaagcg tggccacccg tatggtagga gtgtccaaaa a aaagtaccc    5400 caacccccacc cattggtgcc ctacaatttc aaatgaacct actagttccc a aagactgaa    5460 ggagataagc aagcaaacag gcggctagtt cactccatga tctgagaatc t cctgryact    5520 gataaacgac atcttcaata ctacacttgc aggatccact agt                       5563
```

<210> SEQ ID NO 27
<211> LENGTH: 4811
<212> TYPE: DNA
<213> ORGANISM: Artificial Sequence
<220> FEATURE:
<223> OTHER INFORMATION: Description of Artificial Sequence; Note = Synthetic Construct

<400> SEQUENCE: 27

```
atattttggg ttatggctaa aataattaat gtctaaaacg ggattacgcg t ttttcgtaa     60 agctcaaaga cgcatgtgcc aaaaatagcc ttttattaaa ttgtttggtt a ttaaaatat    120 tattcaactt attttacatc catggaaaga gacatggcct cttctatttg a cctgcatgt    180 gttaaaacga aatgccaaaa taagaaaaa aatgtaattc aacatgtaag g ctattcaaa    240 aacaatacac aggtacaaaa catatctttg ttaatgaaac taatttacag t ttgttttatt    300 aaaacacact ataaatgcca tagaacattt tggagatgca tgcgttatac a ttgcgtgat    360 ttaacagatc aattaaagtc gtattttgcg ccagcatttc aatgggcata a cgacttaat    420 gttttcctct agaatgatta caaatgtgaa agcgaatgtg atgtgattga g ttgaagaat    480 tagttttttt tggaatgccc caaggacgca tgcattagcc cacctgtgct g tttatttaa    540 atcattgact ccaagagctg tcagccacaa aaggagggcg ggcgcgctgt c atcacccat    600 cagatttatg actgccacac aatcattttc cgactaaact aacgccatca t cactcagaa    660 caagaacttc atgagtcgca caagacaagt tataataaat gcattacagc g aatgcatgc    720 acaaacgcga gaaccacttt tgctgcaaaa taatgtggat tgttggttga a atgaaaact    780 gggtgagatg cttttctttc aatccctgtt atccatgctt cagcagagga c aggaggctt    840 gtgactttgc ctgtgcctgt gtctgccccc gagtgccctg tcacaatcta a ttaccgtg    900 agtaaaggac aataccgctt cagctggtct gtgtcattcc ccctatatcc c agtgcctgc    960 ttattttcac aaacccttct cgccgctttt ctgcccccctc ctgccctctt t taaccccac   1020 ggagaatgat aaatgcgcgg tgagggaacg aacgggcaaa gccatttcac g gcacctgtt  1080
```

-continued

```
aattaaggga atgattgcct ccattttttcg ctgagctcgt ttccagcgtg c tccattatt   1140
tgtgatgcga ttaattgaaa gcgaatgtga catcacaacg aacgtgatgt c attgtcgcc   1200
gtcacacagt agaacgacag agttacataa gaaataaagt ctgcatgcat a catttatgc   1260
atggcgtttt aaagaagagc gcacactggg ttagagtcct cggtggggtc a gccacttcg   1320
gtaacacccc aagcattcaa tgctaagccc ttaaaaggac agcgtctttt g ttctaacat   1380
cgagagcacc gggattacca caggtattta gttcaggtat tctctaagaa t atttagccc   1440
taggtgagct gaaccaagag cagtcattag cgctaaaact ggctctgatg g gaagggcta   1500
acacacacac acacacacac acacacacac acacacacat tataataaat g taatgtcat   1560
gtttacaaca actccggcag tgatgctgca tattggcggc gtacatacac t aaatgtttt   1620
aatgtagtct gtaagactag agaatcagaa attaatttac acagaaatta c aaaaataaa   1680
tacatgttta aatagttaat aaacataatt caaatatgta atgtattatc g tgtattta   1740
acattaatgg atgaggtggt tcaaatgcat tttgcacaaa ataaaatcga a gcagcttca   1800
aatcgtaaag ataatagtcg gtagcattga atctgcttta acatttactt t tagcgaagg   1860
ctactttatt aaggaagctc atattaactc ccaatgaatg tctgctattg c ccttttttg   1920
aggtgtagac tgtgtaaaat gcatcactgc acagcaaaat caagcgtcat a ttatcctgt   1980
acattctaat ttgttggctt caggctgcca gggctctttg tgctgtgtag g gccctggc   2040
cagattccag tgtgttaaaa agggatttac gcatctgata ttgtcacaca a taaggacaa   2100
atagcccgtt tgagcatctt tatacaacca acgctgacag aggttctgcg g tttaagtgc   2160
ttagtgttgc atttgtgctt aaattgattg tttggtgttc aaccctcact g gaaaaaaat   2220
cttttgatgc aaatgggtgc gtttagataa aaagaagcaa agcctagaac t aaagcctag   2280
aatttatatt gcactgtaga gtgatggt tatgggaaag ttttttgaga t actgtgggg   2340
cgagtcacg cgtcagagtg gcggccggta ggggctctaa actcgcgctc c aattattgc   2400
ctgtcagtca tcatcgcttt agattagagc atgcggatta aaactcatgc c tttaaataa   2460
taacaacagc gtcaatatta tcaaaaagac acatcacgct tatttaaaat c tacgaaatg   2520
tgttaaagca taatttgtac tactggttga ttgttgtaga cctgaaatcc t gtcagatag   2580
aaatgaacta cccggaccac tggtagttaa gtctctcttg tgttatcttt g attgatcca   2640
accagacaag ctagttaaat taataattta taagcgcaaa gcgttggtac a agcagttag   2700
agggagaaag gtgagaagaa gcaatacaaa gtagctaaat tcacaatgca t tacattgtc   2760
cattttagaa atgaaacacg aggatttaat gttaaatgaa tacagagtag c tataatcag   2820
caatacaaag tagctaaatt cagcaataca agtagctaa attcagcaat a caaagtagc   2880
tatattcagc aatacaaagt agctaaattc agcaatacaa agtagctata t tcagcaata   2940
caaagtagct atattcagca atacaaagta gctaaattca gcaatacaac g tagctatac   3000
tttgtagcta tacactgtat ccattttaga aatgcacacg atgattttct g ttaaaaatc   3060
actgctcatt tgaattagat tatttgaatt ggagcttaca ttgcatgtaa t tagtaagca   3120
aattcggctt aacaaatttg aaacgcgttt tttttctcg actaaattaa t taagaaaat   3180
gtattattga tgggtgcaaa cagtaacaat ttattaaacc ctctatgcaa a tgaggtgtt   3240
cagctgacta acctgcatcc acagtttatc taaacgctta tcaaactaat t ggcgacgtt   3300
ctgtctttct gcctgcggtg ggcgagcctg ctgcttgttt tgccacgaga t aattgtacg   3360
caagaatcaa cgaagctgcc ctaatggcca ccaattggct ttatttggac c tgcccatgc   3420
gacctgtcgg cacctccaag agacgggctc gctattaata tgtaaagtga c gtttgatcg   3480
```

```
cttgaaacgg catacaaaga cagtgttttc acaagaagaa tgtggtgaca a ctcatttaa    3540 aactattaga cgcgcaagaa caatagcccc caatttagag accataaaat a ctcctcccc    3600 aattaatgcc tgaggtgcta ggagttgagt ttgcttgcat taggcacata t ctcatgtga    3660 cacttcagtg ttacaggttt tgttgtttta agctaatgtt aatggtcagg g aacagctcg    3720 taatcacaat atatatttaa aacaaatgat tattatgaat gcaataggcc a aatcgatat    3780 tcattaatag aatagaggca ttttaataca tttctgcaca attaaaaatt a aatataatc    3840 ctgcaagtct ataattatat tattcacatc atttaatgtc ctaaaaataa a tttaaaaaa    3900 tagcattagg ctgcaactta gattttaggc ttttctgtta gcacttgagt a aaaagacat    3960 cattacacac catcaacgtg aagctctaaa aagggtaaaa agatctcaat a aattgctgc    4020 gctgaatgat gagtctctca gctctctgga tgtggagcag taggccgaca g tcgccgtgg    4080 catttcggaa agcatgctgt ccgagccaat ggcagtcagc gcgctctgct a ttggttccc    4140 agggcgctca ctgccagctc gtgtccccgc ccatgttcgt aagatatgga a tctactggc    4200 gccagttccg acagtacaca ggcacaattc attaatgaga cttctctccg c tttagacag    4260 acgcagagtt ttagggagac tttaacaatc gggctgtgga caatttaaac c agtggcgaa    4320 ttacgaacgt caacaggcat cttgaggatt aacattcttt gcgcaggact a acacgggaa    4380 aaataaacgc aggattggag tgctgaaatg caactttgcg ccgtgagtac t tcccgatag    4440 ttatttgaaa ttgcgagcat ttaattgagc gatttaattg attgactaca a aagttagcc    4500 tacttatatt aactgaggcg tcgtcgtgtg aattaagatc tgtcttgcac t gtgtttaac    4560 gtcaacactg agatgcttct atctgttatt ctcttacagg tgtccctggc c acccttgaa    4620 tgcaaagaag caggacctct acactccttc aaaaataaaa gcatgctcag a aagtaaaca    4680 gagcatcgcc acctgaagca ttaagctaac gacagatatt ttaataatct a acggactat    4740 agtggtgctt tcgggtctgt agtgtcaagt aaacttttcc aagcattttc t aagcgcgga    4800 cacttgagat g                                                         4811
```

CELL-LINEAGE SPECIFIC EXPRESSION IN TRANSGENIC ZEBRAFISH

BACKGROUND OF THE INVENTION

The disclosed invention is generally in the field of transgenic fish, and more specifically in the area of transgenic fish exhibiting tissue-specific expression of a transgene.

Transgenic technology has become an important tool for the study of gene and promoter function (Hanahan, *Science* 246:1265–75 (1989); Jaenisch, *Science* 240:1468–74 (1988)). The ability to express, and study the expression of, genes in whole animals can be facilitated by the use of transgenic animals. Transgenic technology is also a useful tool for cell lineage analysis and for transplantation experiments. Studies on promoter function or lineage analysis generally require the expression of a foreign reporter gene, such as the bacterial gene lacZ. Expression of a reporter gene can allow the identification of tissues harboring a transgene. Typically, transgenic expression has been identified by in situ hybridization or by histochemistry in fixed animals. Unfortunately, the inability to easily detect transgene expression in living animals severely limits the utility of this technology, particularly for lineage analysis.

An attractive paradigm for the understanding of gene expression, development, and genetics of animals, especially humans, is to study less complex organisms, such as *Escherichia coli*, Drosophila, and Caenorhabditis. The hope is that understanding of these processes in simple organisms will have relevance to similar processes in mammals and humans. The tradeoff is to accept the disadvantage that an experimental organism is only distantly related to humans for the advantage of easy manipulation, fast generation times, and more straightforward interpretation of results in the experimental organism. The disadvantage of this tradeoff can be lessened by using an organism that is as closely related as possible to mammals while retaining as many of the advantages of less complex organisms. The problem is to identify suitable organisms for such studies, and, more importantly, to develop the tools necessary to manipulate such organisms.

Some examples of cell determination in invertebrates have been shown to occur in progressive waves that are regulated by sequential cascades of transcription factors. Much less is known about such processes in vertebrates. An integrated approach combining embryological, genetic and molecular methods, such as that used to study development in Drosophila (for example, Ghysen et al., *Genes & Dev* 7:723–33 (1993)), would facilitate the identification of the molecular mechanisms involved in specifying neuronal fates in vertebrates, but such an approach has been hampered by a lack of robust genetic and molecular tools for use in vertebrates.

Transgenic technology has been applied to fish for various purposes. For example, transgenic technology has been applied to several commercially important varieties of fish, primarily in an attempt to improve their cultivation. The use of transgenic technology in fish has been reviewed by Moav, Israel *J. of Zoology* 40:441–466 (1994), Chen et al., *Zoological Studies* 34:215–234 (1995), and Iyengar et al., *Transgenic Res.* 5:147–166 (1996).

Stuart et al., *Development* 103:403–412 (1988), describe integration of foreign DNA into zebrafish, but no expression was observed. Stuart et al., *Development* 109:577–584 (1990), describe expression of a transgene in zebrafish from SV40 and Rous sarcoma virus transcription regulatory sequences. Although expression was seen in a pattern of tissues, the expression within a given tissue was variegated. Also, since Stuart et al. (1990) selected transgenics by expression and not by the presence of the transgene, non-expressing transgenics would have been missed by their analysis. Culp et al., *Proc. Natl. Acad. Sci. USA* 88:7953–7957 (1991), describe integration and germ line transmission of DNA in zebrafish. Although the constructs used included the Rous sarcoma virus LTR or SV40 enhancer promoter linked to a lacZ gene, no expression was observed. Bayer and Campos-Ortega, *Development* 115:421–426 (1992), describe integration and expression in zebrafish of a lacZ transgene having a minimal promoter (a mouse heat shock promoter) but no upstream regulatory sequences. The expression obtained depended on the site of integration indicating that endogenous sequences at the site of integration of the fish were responsible for expression. Westerfield et al., *Genes & Development* 6:591–598 (1992), describe transient expression in zebrafish of β-galactosidase from mouse and human Hox gene promoters. Lin et al., *Dev. Biology* 161:77–83 (1994), describe transgenic expression of lacZ in living zebrafish embryos. The transgene linked the enhancer-promoter of the Xenopus elongation factor 1α gene with the lacZ coding sequence. Different lines of transgenic fish exhibited different patterns of expression, indicating that the site of integration may be affecting the pattern of expression. Amsterdam et al., *Dev. Biology* 171:123–129 (1995), and Amsterdam et al., *Gene* 173:99–103 (1996), describe transgenic expression of green fluorescent protein (GFP) in zebrafish. The transgene linked the enhancer-promoter of the Xenopus elongation factor 1α gene with the GFP coding sequence. As in Lin et al., *Dev. Biology* 161:77–83 (1994), different lines of transgenic fish exhibited different patterns of expression, indicating that the site of integration may be affecting the pattern of expression. Although some of the systems described above exhibited patterned expression, none resulted in the transmission of stable tissue-specific expression of a transgene in zebrafish.

It is an object of the present invention to provide transgenic fish having tissue- and developmentally-specific expression of transgenes.

It is another object of the present invention to provide a method of making transgenic fish having tissue- and developmentally-specific expression of transgenes.

It is another object of the present invention to provide a method of identifying compounds that affect expression of fish genes of interest.

It is another object of the present invention to provide a method of identifying the pattern of expression of fish genes of interest.

It is another object of the present invention to provide a method of identifying genes that affect expression of fish genes of interest.

It is another object of the present invention to provide a method of genetically marking mutant fish genes.

It is another object of the present invention to provide a method of identifying fish that have inherited a mutant gene.

It is another object of the present invention to provide a method of identifying enhancers and other regulatory sequences in fish.

It is another object of the present invention to provide a construct that exhibits tissue- and developmentally-specific expression in fish.

BRIEF SUMMARY OF THE INVENTION

Disclosed are transgenic fish, and a method of making transgenic fish, which express transgenes in stable and predictable tissue- or developmentally-specific patterns. The transgenic fish contain transgene constructs with homologous expression sequences. Also disclosed are methods of using such transgenic fish. Such expression of transgenes allow the study of developmental processes, the relationship of cell lineages, the assessment of the effect of specific genes and compounds on the development or maintenance of specific tissues or cell lineages, and the maintenance of lines of fish bearing mutant genes.

BRIEF DESCRIPTION OF THE DRAWINGS

FIG. 4 is a diagram of the structures of GATA-2/GFP transgene constructs for analyzing the expression sequences of the GATA-2 gene. The thick open box represents a 1116 bp fragment of the upstream region of the GATA-2 gene required for neuron-specific expression. The thin open box represents segments of the upstream region of the GATA-2 gene proximal to the transcription start site. The thick line represents the minimal promoter of the Xenopus elongation factor 1α gene. The hatched box represents a segment encoding the modified GFP and including a SV40 polyadenylation signal.

FIG. 5 is a graph of the percent of embryos microinjected with the transgene constructs shown in FIG. 4 that expressed GFP in neurons.

DETAILED DESCRIPTION OF THE INVENTION

Figures 1A, 1B:
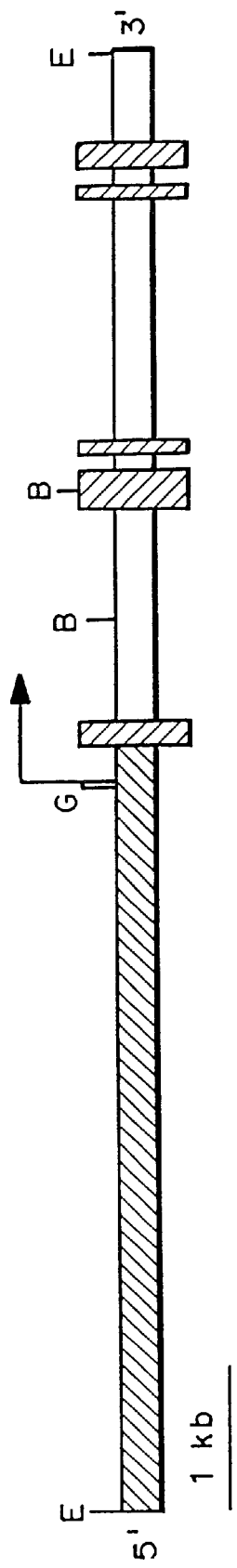
FIG. 1A shows the nucleotide sequence at the exon/intron junctions of the zebrafish GATA-1 locus. The conserved splice sequences are underlined and the intron sequences are listed within parentheses. The amino acids encoded by the exon regions flanking the introns are shown beneath the nucleotide sequence. The upstream splice junction nucleotide sequences are SEQ ID NO:6 (IVS-1), SEQ ID NO:7 (IVS-2), SEQ ID NO:8 (IVS-3), and SEQ ID NO:9 (IVS-4). The downstream splice junction nucleotide sequences are SEQ ID NO:10 (IVS-1), SEQ ID NO:11 (IVS-2), SEQ ID NO:12 (IVS-3), and SEQ ID NO: 13 (IVS-4). The amino acid sequences spanning the introns are SEQ ID NO:14 (IVS-1), SEQ ID NO: 15 (IVS-2), SEQ ID NO:16 (IVS-3), and SEQ ID NO:17 (IVS-4).
FIG. 1B is a diagram of the structure of the zebrafish GATA-1 locus. Exon regions are filled. Intron regions are unfilled. The tall filled boxes represent the coding regions. The arrow indicates the putative transcription start site. EcoRI endonuclease sites are labeled E. BglII endonuclease sites are labeled G. BamHI endonuclease sites are labeled B.

Disclosed are transgenic fish, and a method of making transgenic fish, which express transgenes in stable and predictable tissue- or developmentally-specific patterns. Also disclosed are methods of using such transgenic fish. Such expression of transgenes allow the study of developmental processes, the relationship of cell lineages, the assessment of the effect of specific genes and compounds on the development or maintenance of specific tissues or cell lineages, and the maintenance of lines of fish bearing mutant genes. The disclosed transgenic fish are characterized by homologous expression sequences in an exogenous construct introduced into the fish or a progenitor of the fish.

As used herein, transgenic fish refers to fish, or progeny of a fish, into which an exogenous construct has been introduced. A fish into which a construct has been introduced includes fish which have developed from embryonic cells into which the construct has been introduced. As used herein, an exogenous construct is a nucleic acid that is artificially introduced, or was originally artificially introduced, into an animal. The term artificial introduction is intended to exclude introduction of a construct through normal reproduction or genetic crosses. That is, the original introduction of a gene or trait into a line or strain of animal by cross breeding is intended to be excluded. However, fish produced by transfer, through normal breeding, of an exogenous construct (that is, a construct that was originally artificially introduced) from a fish containing the construct are considered to contain an exogenous construct. Such fish are progeny of fish into which the exogenous construct has been introduced. As used herein, progeny of a fish are any fish which are descended from the fish by sexual reproduction or cloning, and from which genetic material has been inherited. In this context, cloning refers to production of a genetically identical fish from DNA, a cell, or cells of the fish. The fish from which another fish is descended is referred to as a progenitor fish. As used herein, development of a fish from a cell or cells (embryonic cells, for example), or development of a cell or cells into a fish, refers to the developmental process by which fertilized egg cells or embryonic cells (and their progeny) grow, divide, and differentiate to form an adult fish.

The examples illustrate the manner in which transgenic fish exhibiting cell lineage-specific expression can be made and used. The transgenic fish described in the examples, and the transgene constructs used, are particularly useful for early detection of fish expressing the transgene, the study of erythroid cell development, the study of neuronal development, and as a reporter for genetically linked mutant genes.

Tissue-, developmental stage-, or cell lineage-specific expression of a reporter gene from a regulated promoter in the disclosed transgenic fish can be useful for identifying the pattern of expression of the gene from which the promoter is derived. Such expression can also allow study of the pattern of development of a cell lineage. As used herein, tissue-specific expression refers to expression substantially limited to specific tissue types. Tissue-specific expression is not necessarily limited to expression in a single tissue but includes expression limited to one or more specific tissues. As used herein, developmental stage-specific expression refers to expression substantially limited to specific developmental stages. Developmental stage-specific expression is not necessarily limited to expression at a single developmental stage but includes expression limited to one or more specific developmental stage. As used herein, cell lineage-specific expression refers to expression substantially limited to specific cell lineages. As used herein, cell lineage refers to a group of cells that are descended from a particular cell or group of cells. In development, for example, newly specialized or differentiated cells can give rise to cell lineages. Cell lineage-specific expression is not necessarily limited to expression in a single cell lineage but includes expression limited to one or more specific cell lineages. All of these types of specific expression can operate in the same gene. For example, a developmentally regulated gene can be expressed at both specific developmental stages and be limited to specific tissues. As used herein, the pattern of expression of a gene refers to the tissues, developmental stages, cell lineages, or combinations of these in or at which the gene is expressed.

1. Transgene Constructs

Transgene constructs are the genetic material that is introduced into fish to produce a transgenic fish. Such constructs are artificially introduced into fish. The manner of introduction, and, often, the structure of a transgene construct, render such a transgene construct an exogenous construct. Although a transgene construct can be made up of any nucleic acid sequences, for use in the disclosed transgenic fish it is preferred that the transgene constructs combine expression sequences operably linked to a sequence encoding an expression product. The transgenic construct will also preferably include other components that aid expression, stability or integration of the construct into the genome of a fish. As used herein, components of a transgene construct referred to as being operably linked or operatively linked refer to components being so connected as to allow them to function together for their intended purpose. For example, a promoter and a coding region are operably linked if the promoter can function to result in transcription of the coding region.

A. Expression Sequences

Expression sequences are used in the disclosed transgene constructs to mediate expression of an expression product encoded by the construct. As used herein, expression sequences include promoters, upstream elements, enhancers, and response elements. It is preferred that the expression sequences used in the disclosed constructs be homologous expression sequences. As used herein, in reference to components of transgene constructs used in the disclosed transgenic fish, homologous indicates that the component is native to or derived from the species or type of fish involved. Conversely, heterologous indicates that the component is neither native to nor derived from the species or type of fish involved.

Two large scale chemical mutagenesis screens recently produced thousands of zebrafish mutants affecting development (Driever et al., *Development* 123:37–46 (1996); Haffter et al., *Development* 123:1–36 (1996)). Such genes and their expression patterns are of significant interest for understanding the developmental process. Therefore, expression sequences from these genes are preferred for use as expression sequences in the disclosed constructs.

As used herein, expression sequences are divided into two main classes, promoters and enhancers. A promoter is generally a sequence or sequences of DNA that function when in a relatively fixed location in regard to the transcription start site. A promoter contains core elements required for basic interaction of RNA polymerase and transcription factors, and may contain upstream elements and response elements. Enhancer generally refers to a sequence of DNA that functions at no fixed distance from the transcription start site and can be in either orientation. Enhancers function to increase transcription from nearby promoters. Enhancers also often contain response elements that mediate the regulation of transcription. Promoters can also contain response elements that mediate the regulation of transcription.

Enhancers often determine the regulation of expression of a gene. This effect has been seen in so-called enhancer trap constructs where introduction of a construct containing a reporter gene operably linked to a promoter is expressed only when the construct inserts into the domain of an enhancer (O'Kane and Gehring, *Proc. Natl. Acad. Sci. USA* 84:9123–9127 (1987), Allen et al., *Nature* 333:852–855 (1988), Kothary et al., *Nature* 335:435–437 (1988), Gossler et al., *Science* 244:463–465 (1989)). In such cases, the expression of the construct is regulated according to the pattern of the newly associated enhancer. Transgenic constructs having only a minimal promoter can be used in the disclosed transgenic fish to identify enhancers.

Preferred enhancers for use in the disclosed transgenic fish are those that mediate tissue- or cell lineage-specific expression. More preferred are homologous enhancers that mediate tissue- or cell lineage-specific expression. Still more preferred are enhancers from fish GATA-1 and GATA-2 genes. Most preferred are enhancers from zebrafish GATA-1 and GATA-2 genes.

For expression of encoded peptides or proteins, a transgene construct also needs sequences that, when transcribed into RNA, mediate translation of the encoded expression products. Such sequences are generally found in the 5' untranslated region of transcribed RNA. This region corresponds to the region on the construct between the transcription initiation site and the translation initiation site (that is, the initiation codon). The 5' untranslated region of a construct can be derived from the 5' untranslated region normally associated with the promoter used in the construct, the 5' untranslated region normally associated with the sequence encoding the expression product, the 5' untranslated region of a gene unrelated to the promoter or sequence encoding the expression product, or a hybrid of these 5' untranslated regions. Preferably, the 5' untranslated region is homologous to the fish into which the construct is to be introduced. Preferred 5' untranslated regions are those normally associated with the promoter used.

B. Expression Products

Transgene constructs for use in the disclosed transgenic fish can encode any desired expression product, including peptides, proteins, and RNA. Expression products can include reporter proteins (for detection and quantitation of expression), and products having a biological effect on cells in which they are expressed (by, for example, adding a new enzymatic activity to the cell, or preventing expression of a gene). Many such expression products are known or can be identified.

Reporter Proteins

As used herein, a reporter protein is any protein that can be specifically detected when expressed. Reporter proteins are useful for detecting or quantitating expression from expression sequences. For example, operatively linking nucleotide sequence encoding a reporter protein to a tissue specific expression sequences allows one to carefully study lineage development. In such studies, the reporter protein serves as a marker for monitoring developmental processes, such as cell migration. Many reporter proteins are known and have been used for similar purposes in other organisms. These include enzymes, such as β-galactosidase, luciferase, and alkaline phosphatase, that can produce specific detectable products, and proteins that can be directly detected. Virtually any protein can be directly detected by using, for example, specific antibodies to the protein. A preferred reporter protein that can be directly detected is the green fluorescent protein (GFP). GFP, from the jellyfish *Aequorea victoria*, produces fluorescence upon exposure to ultraviolet light without the addition of a substrate (Chalfie et al., *Science* 263:802–5 (1994)). Recently, a number of modified GFPs have been created that generate as much as 50-fold greater fluorescence than does wild type GFP under standard conditions (Cormack et al., *Gene* 173:33–8 (1996); Zolotukhin et al., *J. Virol* 70:4646–54 (1996)). This level of fluorescence allows the detection of low levels of tissue specific expression in a living transgenic animal.

The use of reporter proteins that, like GFP, are directly detectable without requiring the addition of exogenous factors are preferred for detecting or assessing gene expression during zebrafish embryonic development. A transgenic zebrafish embryo, carrying a construct encoding a reporter protein and a tissue-specific expression sequences, can provide a rapid real time in vivo system for analyzing spatial and temporal expression patterns of developmentally regulated genes.

C. Other Construct Sequences

The disclosed transgene constructs preferably include other sequences which improve expression from, or stability of, the construct. For example, including a polyadenylation signal on the constructs encoding a protein ensures that transcripts from the transgene will be processed and transported as mRNA. The identification and use of polyadenylation signals in expression constructs is well established. It is preferred that homologous polyadenylation signals be used in the transgene constructs.

It is also known that the presence of introns in primary transcripts can increase expression, possibly by causing the transcript to enter the processing and transport system for mRNA. It is preferred that an intron, if used, be included in the 5' untranslated region or the 3' untranslated region of the transgene transcript. It is also preferred that the intron be homologous to the fish used, and more preferably homologous to the expression sequences used (that is, that the intron be from the same gene that some or all of the expression sequences are from). The use and importance of these and other components useful for transgene constructs are discussed in Palmiter et al., *Proc. Natl. Acad. Sci. USA* 88:478–482 (1991); Sippel et al., "The Regulatory Domain Organization of Eukaryotic Genomes: Implications For Stable Gene Transfer" in *Transgenic Animals* (Grosveld and Kollias, eds., Academic Press, 1992), pages 1–26; Kollias and Grosveld, "The Study of Gene Regulation in Transgenic Mice" in *Transgenic Animals* (Grosveld and Kollias, eds, Academic Press, 1992), pages 79–98; and Clark et al., *Phil. Trans. R. Soc. Lond. B.* 339:225–232 (1993).

The disclosed constructs are preferably integrated into the genome of the fish. However, the disclosed transgene construct can also be constructed as an artificial chromosome. Such artificial chromosomes containing more that 200 kb have been used in several organisms. Artificial chromosomes can be used to introduce very large transgene constructs into fish. This technology is useful since it can allow faithful recapitulation of the expression pattern of genes that have regulatory elements that lie many kilobases from coding sequences.

2. Fish

The disclosed constructs and methods can be used with any type of fish. As used herein, fish refers to any member of the classes collectively referred to as pisces. It is preferred that fish belonging to species and varieties of fish of commercial or scientific interest be used. Such fish include salmon, trout, tuna, halibut, catfish, zebrafish, medaka, carp, tilapia, goldfish, and loach.

The most preferred fish for use with the disclosed constructs and methods is zebrafish, Danio rerio. Zebrafish are an increasingly popular experimental animal since they have many of the advantages of popular invertebrate experimental organisms, and include the additional advantage that they are vertebrates. Another significant advantage of zebrafish for the study of development and cell lineages is that, like Caenorhabditis, they are largely transparent (Kimmel, *Trends Genet* 5:283–8 (1989)). The generation of thousands of zebrafish mutants (Driever et al., *Development* 123:37–46 (1996); Haffter et al., *Development* 123:1–36 (1996)) provides abundant raw material for transgenic study of these animals. General zebrafish care and maintenance is described by Streisinger, *Natl. Cancer Inst. Monogr.* 65:53–58 (1984).

Zebrafish embryos are easily accessible and nearly transparent. Given these characteristics, a transgenic zebrafish embryo, carrying a construct encoding a reporter protein and tissue-specific expression sequences, can provide a rapid real time in vivo system for analyzing spatial and temporal expression patterns of developmentally regulated genes. In addition, embryonic development of the zebrafish is extremely rapid. In 24 hours an embryo develops rudiments of all the major organs, including a functional heart and circulating blood cells (Kimmel, *Trends Genet* 5:283–8 (1989)). Other fish with some or all of the same desirable characteristics are also preferred.

3. Production of Transgenic Fish

The disclosed transgenic fish are produced by introducing a transgene construct into cells of a fish, preferably embryonic cells, and most preferably in a single cell embryo. Where the transgene construct is introduced into embryonic cells, the transgenic fish is obtained by allowing the embryonic cell or cells to develop into a fish. Introduction of constructs into embryonic cells of fish, and subsequent development of the fish, are simplified by the fact that embryos develop outside of the parent fish in most fish species.

The disclosed transgene constructs can be introduced into embryonic fish cells using any suitable technique. Many techniques for such introduction of exogenous genetic material have been demonstrated in fish and other animals. These include microinjection (described by, for example, Culp et al. (1991)), electroporation (described by, for example, Inoue et al., *Cell. Differ. Develop.* 29:123–128 (1990); Müller et al., *FEBS Lett.* 324:27–32 (1993); Murakami et al., *J. Biotechnol.* 34:35–42 (1994); Müller et al., *Mol. Mar. Biol. Biotechnol.* 1:276–281 (1992); and Symonds et al., *Aquaculture* 119:313–327 (1994)), particle gun bombardment (Zelenin et al., *FEBS Lett.* 287:118–120 (1991)), and the use of liposomes (Szelei et al., *Transgenic Res.* 3:116–119 (1994)). Microinjection is preferred. The preferred method for introduction of transgene constructs into fish embryonic cells by microinjection is described in the examples.

Embryos or embryonic cells can generally be obtained by collecting eggs immediately after they are laid. Depending on the type of fish, it is generally preferred that the eggs be fertilized prior to or at the time of collection. This is preferably accomplished by placing a male and female fish together in a tank that allows egg collection under conditions that stimulate mating. After collecting eggs, it is preferred that the embryo be exposed for introduction of genetic material by removing the chorion. This can be done manually or, preferably, by using a protease such as pronase. A preferred technique for collecting zebrafish eggs and preparing them for microinjection is described in the examples. A fertilized egg cell prior to the first cell division is considered a one cell embryo, and the fertilized egg cell is thus considered an embryonic cell.

After introduction of the transgene construct the embryo is allowed to develop into a fish. This generally need involve no more than incubating the embryos under the same conditions used for incubation of eggs. However, the embryonic cells can also be incubated briefly in an isotonic buffer. If appropriate, expression of an introduced transgene construct can be observed during development of the embryo.

Fish harboring a transgene can be identified by any suitable means. For example, the genome of potential transgenic fish can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgene construct is preferably accomplished by Southern or Northern blotting. Also preferred is detection using polymerase chain reaction (PCR) or other sequence-specific nucleic acid amplification techniques. Preferred techniques for identifying transgenic zebrafish are described in the examples.

4. Identifying the Pattern of Expression of Fish Genes

Identifying the pattern of expression in the disclosed transgenic fish can be accomplished by measuring or identifying expression of the transgene in different tissues (tissue-specific expression), at different times during development (developmentally regulated expression or developmental stage-specific expression), in different cell lineages (cell lineage-specific expression). These assessments can also be combined by, for example, measuring expression (and observing changes, if any) in a cell lineage during development. The nature of the expression product to be detected can have an effect on the suitability of some of these analyses. On one level, different tissues of a fish can be dissected and expression can be assayed in the separate tissue samples. Such an assessment can be performed when using almost any expression product. This technique is commonly used in transgenic animals and is useful for assessing tissue-specific expression.

This technique can also be used to assess expression during the course of development by assaying for the expression product at different developmental stages. Where detection of the expression product requires fixing of the sample or other treatments that destroy or kill the developing embryo or fish, multiple embryos must be used. This is only practical where the expression pattern in different embryos is expected to be the same or similar. This will be the case when using the disclosed transgenic fish having stable and predictable expression.

A more preferred way of assessing the pattern of expression of a transgene during development is to use an expression product that can be detected in living embryos and animals. A preferred expression product for this purpose is the green fluorescent protein. A preferred form of GFP and a preferred technique for measuring the presence of GFP in living fish is described in the examples.

Expression products of the disclosed transgene constructs can be detected using any appropriate method. Many means of detecting expression products are known and can be applied to the detection of expression products in transgenic fish. For example, RNA can be detected using any of numerous nucleic acid detection techniques. Some of these detection methods as applied to transgenic fish are described in the examples. The use of reporter proteins as the expression product is preferred since such proteins are selected based on their detectability. The detection of several useful reporter proteins is described by Iyengar et al. (1996).

In zebrafish, the nervous system and other organ rudiments appear within 24 hours of fertilization. Since the nearly transparent zebrafish embryo develops outside its mother, the origin and migration of lineage progenitor cells can be monitored by following expression of an expression product in transgenic fish. In addition, the regulation of a specific gene can be studied in these fish.

Using zebrafish promoters that drive expression in specific tissues, a number of transgenic zebrafish lines can be generated that express a reporter protein in each of the major tissues including the notochord, the nervous system, the brain, the thymus, and in other tissues (see Table 1). Other important lineages for which specific expression can be obtained include neutral crest, germ cells, liver, gut, and kidney. Additional tissue specific transgenic fish can be generated by using "enhancer trap" constructs to identify expression sequences in fish.

TABLE 1

| Source of Expression Sequences | Tissues/Cell lineages |
| --- | --- |
| GATA-1 | Erythroid progenitor |
| GATA-2 | Hematopoietic stem cells/CNS |
| Tinman | Heart |
| Rag-1 | T and B Cells |
| Globin | Mature red blood cells |
| MEF | Muscle progenitors |
| Goosecoid | Dorsal organizer |
| SCL-1 | Hematopoietic stem cells |
| Rbtn-2 | Hematopoietic stem cells |
| No-tail | Notochord |
| Flk-1 | Vascular endothelia |
| Eve-1 | Ventral/posterior cells |
| Ikaros | Early lymphoid progenitors |
| Pdx-1 | Pancreas |
| Islet-1 | Motoneuron |
| Shh | Multi-tissue induction/Left-right symmetry |
| Twist | Axial mesoderm/Left-right symmetry |
| Krox20 | Brain |
| BMP4 | Ventral mesoderm induction |

5. Identifying Compounds That Affect Expression of Fish Genes

For many genes, and especially for genes involved in developmental processes, it would be useful to identify compounds that affect expression of the genes. The disclosed transgenic fish can be exposed to compounds to assess the effect of the compound on the expression of a gene of interest. For example, test compounds can be administered to transgenic fish harboring an exogenous construct containing the expression sequences of a fish gene of interest operably linked to a sequence encoding a reporter protein. By comparing the expression of the reporter protein in fish exposed to a test compound to those that are not exposed, the effect of the compound on the expression of the gene from which the expression sequences are derived can be assessed.

6. Identifying Genes That Affect Expression of Fish Genes

Numerous mutants have been generated and characterized in zebrafish which affect most developmental processes. The disclosed transgenic fish can be used in combination with these and other mutations to assess the effect of a mutant gene on the expression of a gene of interest. For example, mutations can be introduced into strains of transgenic fish harboring an exogenous construct containing the expression sequences of a fish gene of interest operably linked to a sequence encoding a reporter protein. By comparing the expression of the reporter protein in fish with a mutation to those without the mutation, the effect of the mutation on the expression of the gene from which the expression sequences are derived can be assessed.

The effect of such mutations on specific developmental processes and on the growth and development of specific cell lineages can also be assessed using the disclosed transgenic fish expressing a reporter protein in specific cell lineages or at specific developmental stages.

7. Genetically Marking Mutant Fish Genes

The disclosed transgene constructs can be used to genetically mark mutant genes or chromosome regions. For example, in zebrafish, recent chemical mutagenesis screens have generated more than one thousand different mutants with defects in most developmental processes. If fish carrying a mutation generated in these screens could be more easily identified, a lot of time and labor would be saved. One way to promote rapid identification of fish carrying mutations would be the establishment of balancer chromosomes that carry markers that can be easily identified in living fish. This technology has greatly facilitated the task of identification and maintenance of mutant stocks in Drosophila (Ashburner, Drosophila, A Laboratory Manual(Cold Spring Harbor Laboratory Press, Cold Spring Harbor, N.Y., 1989); Lindsey and Zimm, *The Genome of Drosophila melanogaster* (Academic Press, San Diego, Calif., 1995)). As used herein, genetically marking a gene or chromosome region refers to genetically linking a reporter gene to the gene or chromosome region. Genetic linkage between two genetic elements (such as genes) refers to the elements being in sufficiently close proximity on a chromosome that they do not segregate from each other at random in genetic crosses. The closer the genetic linkage, the more likely that the two elements will segregate together. For genetic marking, it is preferred that the transgene construct segregate with the gene or chromosomal region of interest more than 60% of the time, it is more preferred that the transgene construct segregate with the gene or chromosomal region of interest more than 70% of the time, it is still more preferred that the transgene construct segregate with the gene or chromosomal region of interest more than 80% of the time, it is still more preferred that the transgene construct segregate with the gene or chromosomal region of interest more than 90% of the time, and it is most preferred that the transgene construct segregate with the gene or chromosomal region of interest more than 95% of the time.

Example 1 shows that living transgenic fish carrying insertions of a transgene, in which the zebrafish GATA-1 promoter has been ligated to the green fluorescent protein (GFP) reporter gene, can be identified by simple observation of GFP expression in blood cells. As in Drosophila, zebrafish chromosomal recombination occurs at a significantly lower rate during spermatogenesis than it does during oogenesis. Therefore, a transgene insertion that maps near a chemically induced mutant gene can be crossed into the mutant chromosome through oogenesis and will then remain linked to the mutation in male fish through many generations. This procedure will allow the identification of progeny harboring the mutant gene by simple observation of GFP in blood cells.

In the case of zebrafish, 200 lines carrying the GATA-1/GFP transgene (or another reporter construct), randomly inserted throughout the zebrafish genome should result in an average of 8 insertions in each of the 25 zebrafish chromosomes. This is possible since expression from the disclosed constructs is not limited by effects of the site of insertion and the site of integration is not limited. The insertion sites can be mapped and then crossed through oogenesis into zebrafish lines that carry a mutation that maps nearby. Once established, mutant strains that carry balancer chromosomes can be maintained in male fish.

Although it is preferred that mutant genes be genetically marked, any gene of interest or any chromosome region can be marked, and the maintenance and inheritance of the gene can be monitored, in a similar manner. As used herein, an identified mutant gene is a mutant gene that is known or that has been identified, in contrast to a mutant gene which may be present in an organism but which has not been recognized.

Genetically mapping of mutant genes or transgenes in fish can be performed using established techniques and the principles of genetic crosses. Generally, mapping involves determining the linkage relationships between genetic elements by assessing whether, and to what extent two or more genetic elements tend to cosegregate in genetic crosses.

8. Identifying Fish That Have Inherited a Mutant Gene

Mutant fish in which the mutant gene is marked with an exogenous construct expressing a reporter protein simplify the identification of progeny fish that carry the mutant gene. For example, after a cross, progeny fish can be screened for expression of the reporter protein. Those that express the reporter protein are very likely to have inherited the mutant gene which is genetically linked. Those progeny fish not expressing the reporter protein can be excluded from further analysis.

Although recombination during gametogenesis may result in segregation of the exogenous construct from the mutant gene, this will happen only rarely. Initial screening for fish expressing the reporter protein will still ensure that the majority of such progeny fish will carry the mutant gene. Confirmation of the mutant can be established by subsequent direct testing for the mutant gene.

9. Identifying and Cloning Regulatory Sequences from Fish

The disclosed constructs can also be used as "enhancer traps" to generate transgenic fish that exhibit tissue-specific expression of an expression product. Transgenic animals carrying enhancer trap constructs often exhibit tissue-specific expression patterns due to the effects of endogenous enhancer elements that lie near the position of integration.

Once it is determined that the exogenous construct is operably linked to an enhancer or other regulatory sequence in a fish, the regulatory element can be isolated by re-cloning the transgene construct. Many general cloning techniques can be used for this purpose. A preferred method of cloning regulatory sequences that have become linked to a transgene construct in a fish is to isolate and cleave genomic DNA from the fish with a restriction enzyme that does not cleave the exogenous construct. The resulting fragments can be cloned in vitro and screened for the presence of characteristic transgene sequences. A search for enhancers in zebrafish using a transgene construct having only a promoter operably linked to a sequence encoding a reporter protein has generated a transgenic line that expresses GFP exclusively in hatching gland cells.

A similar procedure can be followed to identify promoters. In this case, a "promoter probe" construct, which lacks any expression sequences, is used. Only if the construct is inserted into the genome downstream of expression sequences will the expression product encoded by the construct be expressed.

10. Identifying Promoters and Enhancers in Cloned Expression Sequences

The linked genomic sequences of clones identified as containing expression sequences, or any other nucleic acid segment containing expression sequences, can then be characterized to identify potential and actual regulatory sequences. For example, a deletion series of a positive clone can be tested for expression in transgenic fish. Sequences essential for expression, or for a pattern of expression, are identified as those which, when deleted from a construct, no longer support expression or the pattern of expression. The ability to assess the pattern of expression of a transgene in fish using the disclosed transgenic fish and methods makes it possible to identify the elements in the regulatory sequences of a fish gene that are responsible for the pattern of expression. The disclosed transgenic fish, since they can be produced routinely and consistently, allow meaningful comparison of the expression of different deletion constructs in separate fish.

An example of the power of this capability is described in Example 2. Application of this system to the study of the GATA-2 promoter has led to identification of enhancer regions that facilitate gene expression specifically in hematopoietic precursors, the enveloping layer (EVL) and the central nervous system (CNS). Through site-directed mutagenesis, it has been discovered that the DNA sequence CCCTCCT is essential for the neuron-specific activity of the GATA-2 promoter. This is described in Example 2.

11. Isolating Cells Expressing an Expression Product

Using cell sorting based on the presence of an expression product, pure populations of cells expressing a transgene construct can be isolated from other cells. Where the transgene construct is expressed in particular cell lineages or tissues, this can allow the purification of cells from that particular lineage. These cells can be used in a variety of in vitro studies. For instance, these pure cell populations can provide mRNA for differential display or subtractive screens for identifying genes expressed in that cell lineage. Progenitor cells of specific tissue could also be isolated. Establishing such cells in tissue culture would allow the growth factor needs of these cells to be determined. Such knowledge could be used to culture non-transgenic forms of the same cells or related cells in other organisms.

Cell sorting is preferably facilitated by using a construct expressing a fluorescent protein or an enzyme producing a fluorescent product. This allows fluorescence activated cell sorting (FACS). A preferred fluorescent protein for this purpose is the green fluorescent protein. The ability to generate transgenic fish expressing GFP in a tissue- and cell lineage-specific manner for different cell types indicates that transgenic fish that express GFP in other types of tissues can be generated in a straightforward manner. The disclosed FACS approach can therefore be used as a general method for isolating pure cell populations from developing embryos based solely on gene expression patterns. This method for isolation of specific cell lineages is preferably performed using constructs linking GFP with the expression sequences of genes identified as being involved in development. Numerous such genes have been or can be identified as mutants that affect development. Cells isolated in this manner should be useful in transplantation experiments.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Example 1

Tissue-specific Expression and Germline Transmission of a Transgene in Zebrafish.

In this example, DNA constructs containing the putative zebrafish expression sequences of GATA-1, an erythroid-specific transcription factor, operatively linked to a sequence encoding the green fluorescent protein (GFP), were microinjected into single-cell zebrafish embryos.

GATA-1, an early marker of the erythroid lineage, was initially identified through its effects upon globin gene expression (Evans and Felsenfeld, Cell 58:877–85 (1989); Tsai et al., Nature 339:446–51 (1989)). Since then GATA-1 has been shown to be a member of a multigene family. Members of this gene family encode transcription factors that recognize the DNA core consensus sequence, WGATAR (SEQ ID NO: 18). GATA factors are key regulators of many important developmental processes in vertebrates, particularly hematopoiesis (Orkin, Blood 80:575–81(1992)). The importance of GATA-1 for hematopoiesis was definitively demonstrated in null mutations in mouse (Pevny et al., Nature 349:257–60 (1991)). In chimeric mice, embryonic stem cells carrying a null mutation in GATA-1, created via homologous recombination, contributed to all non-hematopoietic tissues tested and to a white blood cell fraction, but failed to give rise to mature red blood cells.

In zebrafish, GATA-1 expression is restricted to erythroid progenitor cells that initially occupy a ventral extra-embryonic position, similar to the situation found in other vertebrates (Detrich et al., Proc Natl Acad Sci USA 92:10713–7 (1995)). As development proceeds, these cells enter the zebrafish embryo and form a distinct structure known as the hematopoietic intermediate cell mass (ICM).

Vertebrate hematopoiesis is a complex process that proceeds in distinct phases, at various anatomic sites, during development (Zon, Blood 86:2876–91 (1995)). Although studies on in vitro model systems have generated some insight into hematopoietic development (Cumano et al., Cell 86:907–16 (1996); Kennedy et al., Nature 386:488–493 (1997); Medvinsky and Dzierzak, Cell 86:897–906 (1996); Nakano et al., Science 272:722–4 (1996)), the origin of hematopoietic progenitor cells during vertebrate embryogenesis is still controversial. Therefore, an in vivo model should be useful to determine precisely the cellular and molecular mechanisms involved in hematopoietic development. Such a model could also be used to identify compounds and genes that affect hematopoiesis. In mammals, since embryogenesis occurs internally, it is difficult to carefully observe hematopoietic processes.

Zebrafish have a number of features that facilitate the study of vertebrate hematopoiesis. Because development is external and embryos are nearly transparent, the migration of labeled hematopoietic cells can be easily monitored. In addition, many mutants that are defective in hematopoietic development have been generated (Ransom et al., *Development* 123:311–319 (1996); Weinstein et al., *Development* 123:303–309 (1996)). Zebrafish embryos that significantly lack circulating blood can survive for several days, so downstream effects of mutations upon gene expression deleterious to embryonic hematopoietic development can be characterized. Since the cellular processes and molecular regulation of hematopoiesis are generally conserved throughout vertebrate evolution, results from zebrafish embryonic studies can also provide insight into the mechanisms involved in mammalian hematopoiesis.

Cloning and Sequencing of GATA-1 Genomic DNA

A zebrafish genomic phage library was screened with a $^{32}P$ radiolabeled probe containing a region of zebrafish GATA-2 cDNA that encodes a conserved zinc finger. A number of positive clones were identified. The inserts in these clones were cut with various restriction enzymes. The resulting fragments were subcloned into pBluescript II KS(−) and sequenced. Based on DNA sequence analysis, two phage clones were shown to contain zebrafish GATA-1 sequences. The cDNA sequence of zebrafish GATA-1 is described by Detrich et al., *Proc. Natl. Acad. Sci. USA* 92:10713 (1995). Nucleotide sequence of the GATA-1 promoter region is shown in SEQ ID NO:26.

Plasmid Constructs

Construct G1-(Bgl)-GM2 was generated by ligating a modified GFP reporter gene (GM2) to a 5.4 kb EcoRI/BglII fragment that contains putative zebrafish GATA-1 expression sequences, that is, the 5' flanking sequences upstream of the major GATA-1 transcription start site. GM2 contains 5' wild type GFP and a 3' NcoI/EcoRI fragment derived from a GFP variant, m2, that emits approximately 30 fold greater fluorescence than does the wild type GFP under standard FITC conditions (Cormack et al., *Gene* 173:33–8 (1996)). This construct is illustrated as construct (1) in FIG. 2.

To isolate expression sequences in the 5' untranslated region of GATA-1, a 5.6 kb DNA fragment was amplified by the polymerase chain reaction (PCR) from a GATA-1 genomic subclone using a T7 primer which is complementary to the vector sequence, and a specific primer, Oligo (1), that is complementary to the cDNA sequence just 5' of the GATA-1 translation start. The GATA-1 specific primer contained a BamHI site to facilitate subsequent cloning. The PCR reaction was performed using Expand™ Long Template PCR System (Boehringer Mannheim) for 30 cycles (94° C., 30 seconds; 60° C., 30 seconds; 68° C., 5 minutes). After digestion with BamHI and XhoI, this 5.6 kb DNA fragment was gel purified and ligated to DNA encoding the modified GFP, resulting in construct G1-GM2 (construct (2) in FIG. 2). The construct G1-(5/3)-GM2 was generated by ligating an additional 4 kb of GATA-1 genomic sequences, which contains GATA-1 intron and exon sequences, to the 3' end (following the polyadenylation signal) of the reporter gene in construct G1-GM2. This construct is illustrated as construct (3) in FIG. 2.

Fish and Microinjection

Wild type zebrafish embryos were used for all microinjections. The zebrafish were originally obtained from pet shops (Culp et al., *Proc Natl Acad Sci USA* 88:7953–7 (1991)). Fish were maintained on reverse osmosis-purified water to which Instant Ocean (Aquarium Systems, Mentor, Ohio) was added (50 mg/l). Plasmid DNA G1-GM2 was linearized using restriction enzyme AatII (which cuts in the vector backbone), while plasmid DNA G1-(5/3)-GM2 was excised from the vector by digestion with restriction enzyme SacI, and separated using a low melting agarose gel. DNA fragments were cleaned using GENECLEAN II Kit (Bio101 Inc.) and resuspended in 5 mM Tris, 0.5 mM EDTA, 0.1 M KCl at a final concentration of 50 µg/ml prior to microinjection. Single cell embryos were prepared and injected as described by Culp et al., *Proc Natl Acad Sci USA* 88:7953–7 (1991), except that tetramethyl-rhodamine dextran was included as an injection control. This involved collecting newly fertilized eggs, dechorionating the eggs with pronase (used at 0.5 mg/ml), and injecting DNA. Injection with each construct was done independently 5 to 10 times and the data obtained were pooled.

Fluorescent Microscopic Observation and Imaging

Embryos and adult fish were anesthetized using tricaine (Sigma A-5040) as described previously (Westerfield, The Zebrafish Book (University of Oregon Press, 1995)) and examined under a FITC filter on a Zeiss microscope equipped with a video camera. Images of circulating blood cells were produced by printing out individual frames of recorded videos. Other pictures of fluorescent embryos were generated by superimposing a bright field image on a fluorescent image using Adobe Photoshop software. One month old fish were anesthetized and then rapidly embedded in OCT. Sections of 60 µm were cut using a cryostat and were immediately observed by fluorescence microscopy.

Identification of Germline Transgenic Fish by PCR

DNA isolation, internal control primers and PCR conditions were the same as described by Lin et al. *Dev Biol* 161:77–83 (1994)). Briefly, DNA was extracted from pools of 40 to several hundred dechorionated embryos (obtained from mating a single pair of fish) at 16 to 24 hours of development by vortexing for 1 minute in a buffer containing 4 M guanidium isothiocyanate, 0.25 mM sodium citrate (pH 7.0), and 0.5% Sarkosyl, 0.1 M β-mercaptoethanol. The sample was extracted once with phenol:chloroform: isoamyl alcohol (25:24:1) and total nucleic acid was precipitated by the addition of 3 volumes of ethanol and 1/10 volume sodium acetate (3 M, pH 5.5). The pellet was washed once in 70% ethanol and dissolved in 1×TE (pH 8.0).

Approximately 0.5 µg of DNA was used in a PCR reaction containing 20 mM Tris (pH 8.3), 1.5 mM MgCl$_2$, 25 mM KCl, 100 µg/ml gelatin, 20 pmole each PCR primer, 50 µM each dNTPs, 2.5 U Taq DNA polymerase (Pharmacia). The reaction was carried out at 94° C. for 2.5 minutes for 30 cycles with a 5 minute initial 94° C. denaturation step, and a 7 minute final 72° C. elongation step. Specific primers, Oligos (2) and (3), that were used to detect GFP, generated a 267 bp product. A pair of internal control primers homologous to sequences of the zebrafish homeobox gene, ZF-21 (Njolstad et al., *FEBS Letters* 230:25–30 (1988)), was included in each reaction. This pair of primers should generate a PCR product of 475 bp for all PCR reactions using zebrafish DNA.

Preparation of Embryonic Cells and Flow Cytometry

Embryos were disrupted in Holfereter's solution using a 1.5 ml pellet pestle (Kontes Glass, OEM749521–1590). Cells were collected by centrifugation (400 g, 5 minutes). After digestion with 1×Trypsin/EDTA for 15 minutes at 32° C., the cells were washed twice with phosphate buffered saline (PBS) and filtered through a 40 micron nylon mesh. Fluorescence activated cell sorting (FACS) was performed under standard FITC conditions.

cDNA Synthesis and PCR

Total RNA was extracted from FACS purified cells using the RNA isolation kit, TRIZoL (Bio101). Reverse transcription and PCR (RT-PCR) were performed using the Access RT-PCR System from Promega (Catalog # A1250). Specific primers, Oligos (4) and (5), used to detect the zebrafish GATA-1 cDNA, generated a 410 bp product.

Oligonucleotides
(1) 5'-CCGGATCCTGCAAGTGTAGTATTGAA-3' (GATA-1, promoter antisense; SEQ ID NO:1);
(2) 5'-AATGTATCAATCATGGCAGAC-3' (GM2 sense; SEQ ID NO:2);
(3) 5'-TGTATAGTTCATCCATGCCATGTG-3' (GM2 antisense; SEQ ID NO:3);
(4) 5'-ATGAACCTTTCTACTCAAGCT-3' (GATA-1, cDNA sense; SEQ ID NO:4)
(5) 5'-GCTGCTTCCACTTCCACTCAT-3' (GATA-1, cDNA antisense; SEQ ID NO:5)

Whole-Mount RNA in situ Hybridization

Sense and antisense digoxigenin-labeled RNA probes were generated from a GATA-1 genomic subclone containing the second and third exon coding sequence using a DIG/GeniusTM 4 RNA Labeling Kit (SP6/T7) (Boehinger Mannheim). RNA in situ hybridizations were performed as described (Westerfield, The Zebrafish Book (University of Oregon Press, 1995)).

Genomic Structure of the Zebrafish GATA-1

Two clones containing zebrafish GATA-1 sequences were isolated from a lambda phage zebrafish genomic library as described above. Restriction enzyme mapping indicated that the two overlapping clones contained approximately 35 kb of the GATA-1 locus. To define the promoter of the zebrafish GATA-1 gene, transcription initiation sites for the zebrafish GATA-1 were mapped by primer extension. As in chicken, mouse, human and other species, multiple transcription initiation sites were identified. A major transcription initiation site was mapped 187 bases upstream of the translation start.

Comparison of the GATA-1 genomic structure for human, mouse and chicken suggested that the intron-exon junction sequences of this gene are likely to be conserved throughout vertebrates. Oligonucleotide primers flanking potential GATA-1 introns were designed and used to sequence the zebrafish genomic clones. Sequence analysis revealed that the zebrafish GATA-1 gene consists of five exons and four introns which lie within a 6.5 kb genomic region (FIG. 1). Although the exon-intron number and junction sequences are well conserved between zebrafish and other vertebrates, the zebrafish GATA-1 introns are smaller than in other species.

Transient Expression of GFP Driven by the GATA-1 Promoter in Zebrafish Embryos

Figure 2:
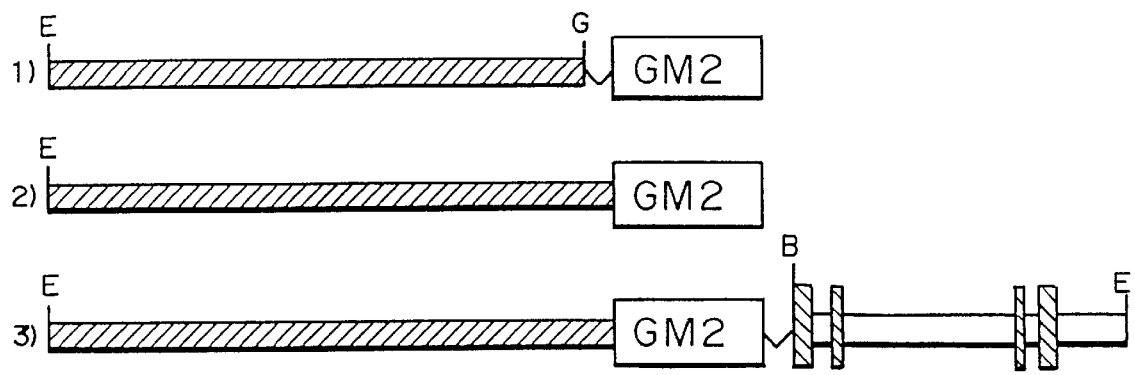
FIG. 2 is a diagram of the structures of three GATA-1/GFP transgene constructs used to make transgenic fish. The filled region to the right of the GM2 box in each construct represents the 5.4 kb or 5.6 kb region of the GATA-1 locus upstream of the GATA-1 coding region. The box labeled GM2 represents a sequence encoding the modified green fluorescent protein. The thin angled lines in constructs (1) and (3) represent vector or linking sequences. EcoRI endonuclease sites are labeled E. BglII endonuclease sites are labeled G. BamHI endonuclease sites are labeled B. In construct (3), the BamHI/EcoRI fragment on the right side is the downstream BamHI/EcoRI fragment of the GATA-1 locus.

Based on the zebrafish GATA-1 genomic structure, three GFP reporter gene constructs were generated (FIG. 2). Construct G1-(Bgl)-GM2 was generated by ligation of a modified GFP reporter gene (GM2) to a 5.4 kb EcoRI/BglII fragment that contains the 5' flanking sequences upstream of the major GATA-1 transcription start site. Construct G1-GM2 contained a 5.6 kb region upstream of the translation start of GATA-1. The third construct, G1-(5/3)-GM2, was generated by ligating an additional 4 kb of GATA-1 genomic sequences, which contain intron and exon sequences, to the 3' end of the reporter gene in construct G1-GM2. Each construct was microinjected into the cytoplasm of single cell zebrafish embryos. GFP reporter gene expression in the embryos was examined at a number of distinct developmental stages by fluorescence microscopy.

GFP expression was observed in embryos injected with either construct G1-GM2 or construct G1-(5/3)-GM2 as early as 80% epiboly, approximately 8 hours post fertilization (pf). At that time, GFP positive cells were restricted to the ventral region of the injected embryos. At 16 hours pf, GFP expression was clearly visible in the developing intermediate cell mass (ICM), the earliest hematopoietic tissue in zebrafish. After 24 hours pf, GFP positive cells were observed in circulating blood and could be continuously observed in circulating blood for several months. During the first five days pf, examination of circulating blood revealed two distinct cell populations with different levels of GFP expression. One cell type was larger and brighter; the other smaller and less bright. No significant difference in GFP expression levels was detected between embryos injected with either construct G1-GM2 or G1-(5/3)-GM2. However, injection of construct G1-(Bgl)-GM2 yielded very weak GFP expression in developing embryos. This result indicated that either the GATA-1 transcription initiation site was removed by BglII restriction digestion, or that the 5' untranslated region of zebrafish GATA-1 is required for high level tissue specific expression of GFP. It is not surprising that a construct lacking the 5' untranslated region of GATA-1 did not generate much GFP expression in microinjected embryos. These regions are often needed for transcript stability. At times, these regions also contain binding sites for regulators of gene expression.

At least 75% of the embryos injected with G1-GM2 or G1-(5/3)-GM2 construct showed some degree of ICM specific GFP expression (Table 2). The number of GFP positive cells in the ICM or in circulation ranged from a single cell to a few hundred cells. Less than 7% of these embryos showed GFP expression in non-hematopoietic tissues, usually limited to fewer than ten cells per embryo. Non-specific expression of GFP was usually observed in the notochord, muscle, and enveloping cell layers, and was limited to no more than 10 cells per embryo. These observations indicated that a genomic GATA-1 fragment extending approximately 5.6 kb upstream from the GATA-1 translation start site ligated to GFP sufficed to recapitulate the embryonic pattern of GATA-1 expression in zebrafish.

TABLE 2

| Constructs | No. observed embryos | No. embryos with GFP expression in ICM (%) | No. embryos with strong GFP expression in ICM (%)[a] | No. embryos with non-specific expression GFP (%) |
|---|---|---|---|---|
| G1-GM2 | 336 | 274 (81.5%) | 177 (52.7%) | 15 (4.5%) |
| G1-GM2(5/3) | 248 | 187 (75.4%) | 150 (60.5%) | 16 (6.5%) |
| G1(BglII)-GM2 | 370 | 0 (0%) | 0 (0%) | 19 (5.1%) |

[a]Strong GFP expression means that each embryo has more than 10 green fluorescent cells in the ICM.

GFP expression in Germline GATA-1/GFP Transgenic Zebrafish

Microinjected zebrafish embryos were raised to sexual maturity and mated. Progeny were tested by PCR to determine the frequency of germline transmission of the GATA-1/GFP transgene. Nine of six hundred and seventy two founder fish have transmitted GFP to the F1 generation. Examination of these fish by fluorescence microscopy revealed that seven of eight lines expressed GFP in the ICM and in circulating blood cells. GFP expression patterns in the ICM were consistent with the RNA in situ hybridization patterns previously observed for GATA-1 mRNA expression in zebrafish (Detrich et al., Proc Natl Acad Sci USA 92:10713–7 (1995)). In the two lines where F2 transgenic fish have been obtained, GFP expression in blood cells was observed in 50% of the progeny when a transgenic F2 was mated to a non-transgenic fish. This indicated that GFP was transmitted to progeny in a Mendelian fashion. Southern blot analysis showed that GFP transgene insertions occurred at different sites in these two lines. In one line, transgenic fish apparently carry 4 copies of the transgene and in the other line, 7 copies.

Blood cells were collected from 48 hour transgenic fish by heart puncture and a blood smear was observed by fluorescence microscopy. Two distinct populations of fluorescent cells were observed in these smears. As in the circulation of embryos that transiently express GFP, one cell population was observed that was large and bright and another that was smaller and less bright. Although the blood cells collected from adult transgenic zebrafish showed some variability in fluorescence intensity, they appeared to have uniform size. Blood cells collected from non-transgenic fish showed no fluorescence.

In two day old transgenic zebrafish, weak GFP expression was observed in the heart. GFP expression was also observed in the eyes and, in three of seven transgenic lines, in some neurons of the spinal cord. Expression in the eyes peaked between 30 and 48 hours pf and became extremely weak by day 4. It is thought that expression of GFP in eyes and neurons may replicate the authentic GATA-1 expression pattern.

Examination of GFP expression in tissues of one month old fish showed that the head kidney contained a large number of fluorescent cells. This result suggests that the kidney is the site of adult erythropoiesis in zebrafish. It has been reported that GATA-1 is expressed in the testes of mice. Expression of GFP was not found in testes dissected from adult fish. It is possible that the disclosed GATA-1 transgene constructs lack an enhancer required for testis expression of GATA-1. Other tissues including brain, muscle and liver had no detectable level of GFP expression.

FACS Analysis of GATA-I/GFP Transgenic Fish

GFP expression in GATA-1/GFP transgenic fish allowed isolation of a pure population of the earliest erythroid progenitor cells for in vitro studies by fluorescence activated cell sorting. F1 transgenic embryos were collected at the onset of GFP expression and cell suspensions were prepared. Approximately 3.6% of the cell populations of whole transgenic fish were fluorescence positives as compared to 0.12% in the non-transgenic controls. Based on the number of embryos used, FACS analysis suggested that there are approximately three hundred erythroid progenitor cells per embryo at 14 hours pf.

To determine whether the FACS purified cells are enriched for GATA-1, RNA was isolated from these cells and GATA-1 mRNA levels were determined by RT-PCR. The results indicated that these cells were highly enriched for GATA-1 mRNA.

Erythroid specific expression was observed in living embryos during early development. Fluorescent circulating blood cells were detected in microinjected embryos 24 hours after fertilization and could still be observed in two month old fish. Germline transgenic fish obtained from the injected founders continued to express GFP in erythroid cells in the F1 and F2 generations. The GFP expression patterns in transgenic fish were consistent with the RNA in situ hybridization pattern generated for GATA-1 mRNA expression. These transgenic fish allowed isolation, by fluorescence activated cell sorting, the earliest erythroid progenitor cells from developing embryos. Using constructs containing other zebrafish promoters and GFP, it will be possible to generate transgenic fish that allow continuous visualization of the origin and migration of any lineage specific progenitor cells in a living embryo.

The results described in this example indicate that monitoring GFP expression can be a more sensitive method than RNA in situ detection by which to determine gene expression patterns. For instance, in the disclosed GATA-1/GFP transgenic fish, GFP expression in circulating blood allowed two types of cells to be distinguished. One cell type was larger and brighter; the other smaller and less bright. There were fewer of the larger, brighter cell type. These cells are believed to be erythroid precursors while the more abundant, smaller cells are believed to be fully differentiated erythrocytes. Preliminary cell transplantation experiments with embryonic blood cells have shown that they contain a cell population that has long-term proliferation capacity.

In two day old transgenic zebrafish, GFP expression was observed in the heart. In adult transgenic zebrafish, GFP expression was observed in the kidney. By histological methods, it has been shown that the heart endocardium is a transitional site for hematopoiesis in embryonic zebrafish and that the kidney is the site of adult hematopoiesis (Al-Adhami and Kunz, *Develop. Growth and Differ.* 19:171–179 (1977)). The results in GATA-1/GFP transgenic fish support these observations.

The GFP expression seen in the eyes and neurons of embryonic transgenic fish may be due to a lack of a transcriptional silencer in the transgene constructs. It seems unlikely that the GFP expression in the eyes is due to positional effects caused by the sites of insertion since all seven transgenic lines have GFP expression in embryonic fish eyes.

Using fluorescence activated cell sorting, pure populations of hematopoietic progenitor cells were isolated from the ICM of transgenic zebrafish. Since approximately $10^7$ cells can be sorted per hour, $10^5$ to $10^6$ purified ICM cells can be obtained in a few hours. These cells, which are derived from the earliest site of hematopoiesis in zebrafish, can be used in a variety of in vitro studies. For instance, these pure cell populations can provide mRNA for differential display or subtractive screens for identifying novel hematopoietic genes. Erythroid precursors obtained from the ICM might also be established in tissue culture. This would allow the growth factor needs of these cells to be determined.

The approach to obtaining and studying transgene expression in erythroid cells described above is generally applicable to the study of any developmentally regulated process. This approach can also be applied to the identification of cis-acting promoter elements that are required for tissue specific gene expression (see Example 2). The analysis of promoter activity in a whole animal is desirable since dynamic temporal and spatial changes in a cellular microenvironment can be only poorly mimicked in vitro. The ease of generating and maintaining a large number of transgenic zebrafish lines makes obtaining statistically significant results practical. Finally, transgenic zebrafish that express GFP in specific tissues provide useful markers for identifying mutations that affect these lines in genetic screens. Given the genetic resources and embryological methods available for zebrafish, transgenic zebrafish exhibiting tissue-specific GFP expression is a very valuable tool for dissecting developmental processes.

Example 2

Identification of Enhancers in GATA-2 Expression Sequences

A large number of studies have shown that neuronal cell determination in invertebrates occurs in progressive waves that are regulated by sequential cascades of transcription factors. Much less is known about this process in vertebrates. It was realized that an integrated approach combining embryological, genetic and molecular methods, such as that used to study neurogenesis in Drosophila (Ghysen et al., Genes & Dev 7:723–33 (1993)), would facilitate the identification of the molecular mechanisms involved in specifying neuronal fates in vertebrates. The following is an example of identification of cis-acting sequences that control neuron-specific gene expression in a vertebrate. Such identification is an initial step toward unraveling similar cascades in a vertebrate.

Transcription factors bind to cis-acting DNA sequences (sometimes referred to as response sequences) to regulate transcription. Often these transcription factors are members of multigene families that have overlapping, but distinct, expression patterns and functions. The transcription factor GATA-2 is a member of such a gene family (Yamamoto et al., Genes Dev 4:1650–62 (1990)). Each member of the GATA gene family is characterized by its ability to bind to cis-acting DNA elements with the consensus core sequence WGATAR (Orkin, Blood 80:575–81 (1992); SEQ ID NO:18). All protein products of the GATA family contain two copies of a highly conserved structural motif, commonly known as a zinc finger, which is required for DNA binding (Martin and Orkin, Genes Dev 4:1886–98 (1994)). Six members of the GATA family have been identified in vertebrates (Orkin, Blood 80:575–81 (1992), Orkin, Curr Opin Cell Biol 7:870–7 (1995)). Pannier, another member of the GATA gene family, is expressed in Drosophila neuronal precursors and inhibits expression of achaete-scute, a gene complex that plays a critical role in neurogenesis in Drosophila (Ramain et al., Development 119:1277–91 (1993)).

In chicken and mouse, the transcription factor GATA-2 is expressed in hematopoietic precursors, immature erythroid cells, proliferating mast cells, the central nervous system (CNS), and sympathetic neurons (Yamamoto et al., Genes & Dev 4:1650–62 (1990), Orkin, Blood 80:575–81 (1992), Jippo et al., Blood 87:993–8 (1996)). Studies in zebrafish (Detrich et al., Proc Natl Acad Sci USA 92:10713–7 (1995)) and Xenopus (Zon et al., Proc Natl Acad Sci USA 88:19642–6 (1991), Kelley et al., Dev Biol 165:193–205 (1994)) have also shown that GATA-2 expression is restricted to hematopoietic tissues and the CNS. Homozygous null mutants, created in mouse via homologous recombination, have profound deficits in all hematopoietic lineages (Tsai et al., Nature 371:221–6 (1994)). The role played by GATA-2 in neuronal tissue of these mice has not been carefully examined, perhaps because the embryos die before day E11.5. Analysis of GATA-2 expression in chick embryonic neuronal tissue after notochord ablation has suggested that GATA-2 plays a role in specifying a neurotransmitter phenotype (Groves et al., Development 121:887–901 (1995)). In addition, GATA factors are required for activity of the neuron-specific enhancer of the gonadotropin-releasing hormone gene (Lawson et al., Mol Cell Biol 16:3596–605 (1996)).

The effects of various hematopoietic growth factors on GATA-2 expression has been carefully studied in tissue culture systems (Weiss et al., Exp Hematol 23:99–107 (1995)) and some growth factors have been shown to have dramatic effects on early embryonic GATA-2 expression (Walmsley et al., Development 120:2519–29 (1994), Maeno et al., Blood 88:1965–72 (1996)). In addition, nuclear translocation of a maternally supplied CCAAT binding transcription factor has been shown to be necessary for the onset of GATA-2 transcription at the mid-blastula transition in Xenopus (Brewer et al., Embo J 14:757–66 (1995)). However, prior to the disclosed work, nothing was known about the mechanisms that control neuron-specific expression of this gene.

Cloning and Sequencing of 5' Part of GATA-2 Genomic DNA

A zebrafish genomic phage library was screened with the conserved zinc finger domain of zebrafish GATA-2 cDNA radiolabeled with $^{32}$P. Two positive clones, λGATA-21 and λGATA-22, were identified. Restriction fragments of λGATA-21 were subcloned into pBluescript II KS(-). DNA sequence of the resulting clones was obtained from -4807 to +2605 relative to the GATA-2 translation start. Nucleotide sequence of the GATA-2 promoter region is shown in SEQ ID NO:27. Unless otherwise indicated, positions within the GATA-2 clones use this numbering. The 7.3 kb region upstream of the translation start in γGATA-21 was amplified by the polymerase chain reaction (PCR) using Expand™ Long Template PCR System (Boehringer Mannheim) for 25 cycles (94° C. ,30 seconds; 68° C., 8 minutes). Primers used were a T7 primer and a primer specific for sequences 5' to the GATA-2 translation start site (5'-ATGGATCCTCAAGTGTCCGCGCTTAGAA-3'; SEQ ID NO:19). The GATA-2 specific primer contained a BamHI site to facilitate subsequent cloning. The PCR product (P1) was cloned into the SmaI/BamHI sites of pBluescript II KS(-).

Plasmid Constructs

Figure 3:
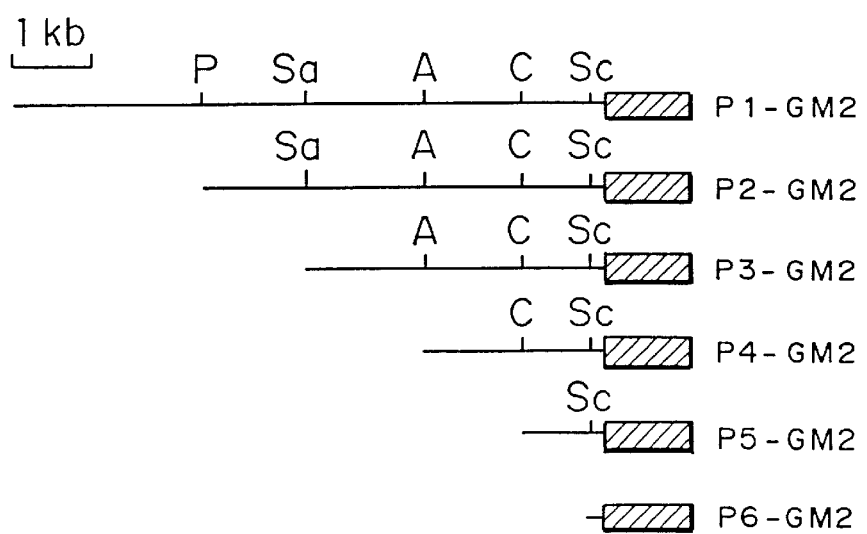
FIG. 3 is a diagram of the structures of GATA-2/GFP transgene constructs for analyzing the expression sequences of the GATA-2 gene. The line represents all or upstream deleted portions of a 7.3 kb region upstream of the translation start site in the zebrafish GATA-2 gene. The hatched box represents a segment encoding the modified GFP and including a SV40 polyadenylation signal. Tick marks labeled P, Sa, A, C, and Sc indicates restriction sites PstI, SacI, AatII, ClaI and ScaI, respectively, in the 7.3 kb region.

The 7.3 kb DNA fragment containing the putative GATA-2 expression sequences (P1) was ligated to a modified GFP reporter gene (GM2, described above), resulting in construct P1-GM2 (FIG. 3). Based on P1-GM2, constructs containing successive 5' deletions in the region upstream of the transcription start site were generated using the restriction sites PstI, SacI, AatII, ClaI and ScaI in this upstream region (FIG. 3). Constructs nsP5-GM2 and nsP6-GM2 were generated by ligating the 1116 bp fragment containing the GATA-2 neuron-specific enhancer from -4807 to -3690 to P5-GM2 and P6-GM2, respectively (FIG. 4). The same fragment containing the neuron-specific enhancer was also ligated to a 243 bp SphI/BamHI fragment of the Xenopus elongation factor 1α (EF 1α) minimal promoter that had previously been ligated to the GM2 gene, resulting in construct ns-XS-GM2 (FIG. 4). The EF 1α minimal promoter has been described in Johnson and Krieg, Gene 147:223–6 (1994).

PCR Mapping of Neuron-Specific Enhancer

PCR technology was exploited to create a deletion series within the 1116 bp neuron-specific enhancer using nsP5-GM2 as a template. A total of 10 specific 22-mer primers were synthesized. These included ns4647, ns4493, ns4292, ns4092, ns3990, ns3872, ns3851, ns3831, ns3800 and ns3789, in which the numbers refer to the positions of their 5' end base in the GATA-2 genomic sequence. A T7 primer was also used in the PCR reactions. The amplified fragments all contained the GM2 gene and SV40 polyadenylation signal in addition to the GATA-2 expression sequences. PCR reactions were performed using Expand™ Long Template PCR System (Boehringer Mannheim) for 25 cycles (94° C., 30 seconds; 55° C., 30 seconds; 72° C., 2 minutes). The PCR products were purified with GENECLEAN II Kit (Bio 101 Inc.) and subsequently used for microinjection.

After a 31 bp neural-specific enhancer was identified, five additional primers, each containing 2 or 3 mutant bases relative to the wild type enhancer sequence, were designed. These primers are (the mutant bases are underlined):

```
ns3831    5'-TCTGCGCCGCTTTCTGCCCCCTCCTGCCCTCTT-3' (SEQ ID NO:20)

ns3831M1  5'-TCTGCGAAGCTTTCTGCCCCCTCCTGCCCTCTT-3' (SEQ ID NO:21)

ns3831M2  5'-TCTGCGCCGCTTTCTGAACCCTCCTGCCCTCTT-3' (SEQ ID NO:22)

ns3831M3  5'-TCTGCGCCGCTTTCTGCCAACTCCTGCCCTCTT-3' (SEQ ID NO:23)

ns3831M4  5'-TCTGCGCCGCTTTCTGCCCCAAACTGCCCTCTT-3' (SEQ ID NO:24)

ns3831M5  5'-TCTGCGCCGCTTTCTGCCCCCTCCTGCCCTCTT-3' (SEQ ID NO:25)
```

These primers were used in conjunction with the T7 primer for PCR amplification of the target sequence using the nsP5-GM2 as the template. PCR conditions were identical to those described above.

Microinjection of Zebrafish

Wild-type zebrafish were used for all microinjections. Plasmid DNA was linearized using single-cut restriction sites in the vector backbone, purified using GENECLEAN II Kit (Bio 101 Inc.), and resuspended in 5 mM Tris, 0.5 mM EDTA, 0.1 M KCl at a final concentration of 100 µg/ml. Single cell embryos were microinjected as described above. Each construct was injected independently 2 to 5 times and the data obtained were pooled.

Fluorescent Microscopic Observation

Embryos were anesthetized using tricaine as described above and examined under a FITC filter on a Zeiss microscope equipped with a video camera. Pictures showing GFP positive cells in living embryos were generated by superimposing a bright field image on a fluorescent image using Adobe Photoshop software.

Whole-Mount RNA in situ Hybridization

Sense and antisense digoxigenin-labeled RNA probes were generated from a GATA-2 cDNA subclone containing a 1 kb fragment of the 5' coding sequence using DIG/Genius™ 4 RNA Labeling Kit (SP6/T7) (Boehinger Mannheim). RNA in situ hybridizations were performed as described by Westerfield (*The Zebrafish Book* (University of Oregon Press, 1995)).

Isolation of GATA-2 Genomic DNA

Two GATA-2 positive phage clones, λGATA-21 and γGATA-22, were identified as described above. Preliminary restriction analysis suggested that λGATA-21 contained a large region upstream of the translation start codon. 7412 bp of this clone was sequenced from −4807 to +2605 relative to the translation start site. The putative GATA-2 expression sequences (P1) containing approximately 7.3 kb upstream of the translation start site from the λGATA-21 was subcloned into a plasmid vector for expression studies.

Expression Pattern of a Modified GFP Gene Driven by the Putative GATA-2 Promoter in Zebrafish Embryos The construct P1-GM2 was generated by ligation of a modified GFP reporter gene (GM2) to P1 (FIG. 3). This construct was injected into the cytoplasm of single cell zebrafish embryos and GFP expression in the microinjected embryos was examined at a number of distinct developmental stages by fluorescence microscopy.

GFP expression was initially observed by fluorescence microscopy at the 4000 cell stage at about 4 hours post-injection (pi). At the dorsal shield stage (6 hours pi), GFP expression was observed throughout the prospective ventral mesoderm and ectoderm but expression in the dorsal shield was extremely rare. At 16 hours pi, GFP expression was observed in the developing intermediate cell mass (ICM), the early hematopoietic tissue of zebrafish. In addition, GFP expression could be seen in superficial EVL cells at 4 hours pi. Expression in the EVL peaked between 24 and 48 hours pi and became extremely weak by day 7. GFP expression in neurons, including extended axons, was first observed at 30 hours pi and was maintained at high levels through at least day 8.

Embryos injected with the P1-GM2 construct expressed GFP in a manner restricted to hematopoietic cells, EVL cells, and the CNS. The GFP expression patterns in gastrulating embryos, in the blood progenitor cells, and in neurons were consistent with the RNA in situ hybridization patterns previously generated for GATA-2 mRNA expression in zebrafish (Detrich et al., *Proc Natl Acad Sci USA* 92:10713–7 (1995)). However, GATA-2 expression in EVL has not been detected by RNA in situ hybridizations.

More than 95% of the embryos injected with P1-GM2 had tissue specific GFP expression (Table 3). About 5% of these embryos had non-specific GFP expression, limited to fewer than five cells per embryo. These observations indicated that the DNA fragment extending approximately 7.3 kb upstream from the GATA-2 translation start site sufficed to correctly generate the embryonic tissue-specific pattern of GATA-2 gene expression.

TABLE 3

| Construct | No. embryos observed | No. embryos with expression | No. embryos with circulating blood expression (%) | No. embryos with neuronal expression (%) | No. embryos with EVL expression (%) |
|---|---|---|---|---|---|
| P1-GM2 | 141 | 135 | 3 (2.13) | 106 (75.2) | 130 (92.2) |
| P2-GM2 | 198 | 177 | 32 (15.7) | 136 (68.7) | 175 (88.4) |
| P3-GM2 | 303 | 291 | 29 (9.6) | 0 (0) | 277 (91.4) |
| P4-GM2 | 143 | 126 | 21 (14.7) | 0 (0) | 118 (82.5) |
| P5-GM2 | 139 | 90 | 16 (11.5) | 0 (0) | 20 (14.4) |
| P6-GM2 | 138 | 44 | 2 (1.4) | 0 (0) | 11 (8.0) |

Gross Mapping of Tissue-Specific Enhancers

To identify the portions of the GATA-2 expression sequences that are responsible for regulating tissue specific gene expression, several constructs containing deletions in the promoter were generated (FIG. 3). Naturally occurring restriction sites were used to create a series of gross deletions in the expression sequence region. Each construct was individually microinjected into single cell embryos. The developing embryos were observed by fluorescence microscopy at regular intervals for several days.

Embryos injected with P2-GM2, which contains GATA-2 sequences from −4807 to +1, expressed GFP in a manner similar to embryos injected with the original construct, P1-GM2 (Table 3). At 48 hr pi, GFP expression was observed in circulating blood cells, the CNS and the EVL. However, careful observation of the injected embryos at 16 hr pi revealed that expression in the posterior end of the ICM was nearly abolished. This suggested that an enhancer for GATA-2 expression in early hematopoietic progenitor cells may reside in the deleted region. Expression of GFP in circulating blood cells increased from approximately 2% to 16%, suggesting that a potential repressor for expression of GATA-2 in erythrocytes may also reside in the deleted region.

Embryos injected with P3-GM2, which contains GATA-2 sequences from −3691 to +1, expressed GFP in circulating blood cells and in the EVL, but did not express in the CNS. Embryos injected with other constructs that lack the deleted 1116 bp region, extending from −4807 to −3692, also had no GFP expression in the CNS (Table 3). It was concluded that the 1116 bp region, extending from −4807 to −3692, contained a neuron-specific enhancer element.

Embryos injected with P4-GM2, which contains GATA-2 sequences from −2468 to +1, had a GFP expression pattern similar to those injected with P3-GM2. Injection with P5-GM2, which contains GATA-2 sequences from −1031 to +1, resulted in a sharp drop with respect to percentage of embryos expressing GFP in the EVL, but GFP expression in circulating blood cells was unaffected. This indicates that the 1437 bp region, extending from −2468 to −1032, contains an EVL-specific enhancer. The 1031 bp segment present in P5-GM2 may represent the minimal expression sequences necessary for the maintenance of tissue specific expression of GATA-2.

Neuron-Specific Enhancer Activity

To confirm the neuron-specific enhancer activity of the 1116 bp region that spans from −4807 to −3692 of GATA-2, nsP5-GM2 was constructed by ligating the 1116 bp fragment to P5-GM2, which contain the 1031 bp region upstream of the translation start of GATA-2 gene operably linked to a sequence encoding GM2 (FIG. 4). Approximately 70% of the embryos injected with nsP5-GM2 had GFP expression in the CNS (FIG. 5), while no embryos injected with P5-GM2 had GFP expression in the CNS as noted in Table 3. This indicates that the 1116 bp region can effectively direct neuron-specific expression.

To determine whether the 1116 bp neuron-specific enhancer activity was context dependent, the construct ns-Xs-GM2 (FIG. 4) was generated by ligating the enhancer to the Xenopus elongation factor 1α minimal promoter (Johnson and Krieg, Gene 147:223–6 (1994)) operably linked to the sequence encoding GM2 (Xs-GM2; FIG. 4). When injected with Xs-GM2, embryos expressed GFP in various tissues including muscle, notochord, blood cells and melanocytes. However, no GFP expression was observed in the CNS (FIG. 5). Injection with ns-XS-GM2 resulted in 8.5% of the embryos having GFP expression in the CNS, far less than obtained by injection with nsP5-GM2 (FIG. 5). Another construct, nsP6-GM2 (FIG. 4), had an additional 653 bp deletion in the GATA-2 minimal expression sequence, extending from −1031 to −378. Injection of nsP6-GM2 resulted in 6.2% of embryos expressing GFP in the CNS (FIG. 5). Injection with P6-GM2 resulted in no GFP expression in the CNS (Table 3). These results suggests that the 1116 bp enhancer has some ability to confer neuronal specificity on a heterogeneous promoter, but requires proximal elements within its own promoter to exert its full activity.

Fine Mapping of a Neuron-Specific Cis-Acting Regulatory Element

Figure 6:
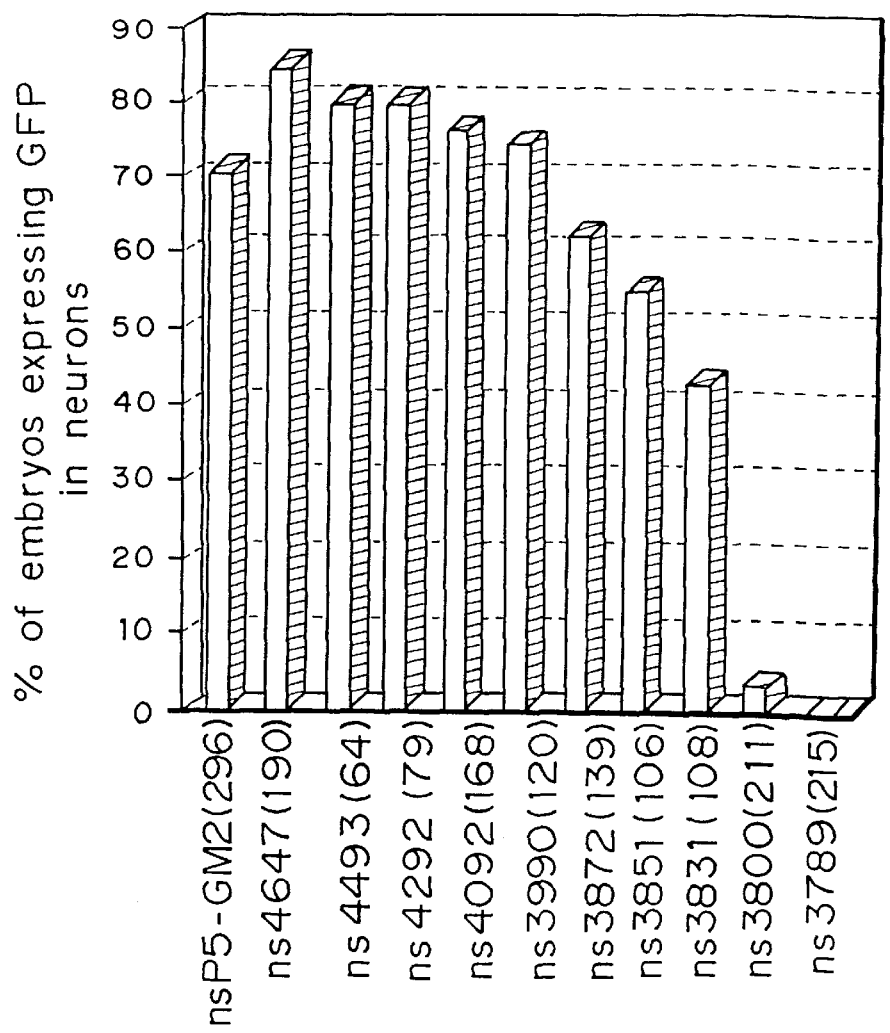
FIG. 6 is a graph of the percent of embryos microinjected with transgene constructs that expressed GFP in neurons. The transgene constructs were nsP5-GM2 and truncated forms of nsP5-GM2.

To precisely map the putative neuron-specific enhancer, a series of constructs containing progressive deletions in the 1116 bp DNA fragment was generated by PCR, using nsP5-GM2 as the template. The PCR products obtained were used directly for microinjection. The first deletion series included ns4647, ns4493, ns4292, ns4092 and ns3990 (where the number indicates the upstream endpoint of the deleted fragment). Microinjection of all 5 mutants gave a similar percentage of embryos having GFP expression in the CNS (FIG. 6). This indicated that a neuron-specific enhancer resides within the 298 bp sequence (from −3990 to −3692) contained in ns3990.

Next, two additional deletion constructs, ns3872 and ns3789, were generated. As shown in FIG. 6, over 60% of embryos injected with ns3872 had GFP expression in the CNS, while embryos injected with ns3789 lacked GFP expression in the CNS. This indicated that the neuron-specific enhancer element was located within a 83 bp sequence from −3872 to −3790.

Injection of embryos with three additional deletion constructs ns3851, ns3831 and ns3800 allowed localization of the neuron-specific enhancer element to a 31 bp pyrimidine-rich sequence. This element has the sequence 5'-TCTGCGCCGCTTTCTGCCCCCTCCTGCCCTC-3' (nucleotides 1 to 31 of SEQ ID NO:20), which extends from −3831 to −3801 within the GATA-2 genomic DNA.

Site Directed Mutagenesis within Neuron-Specific Enhancer Element

Figure 7:
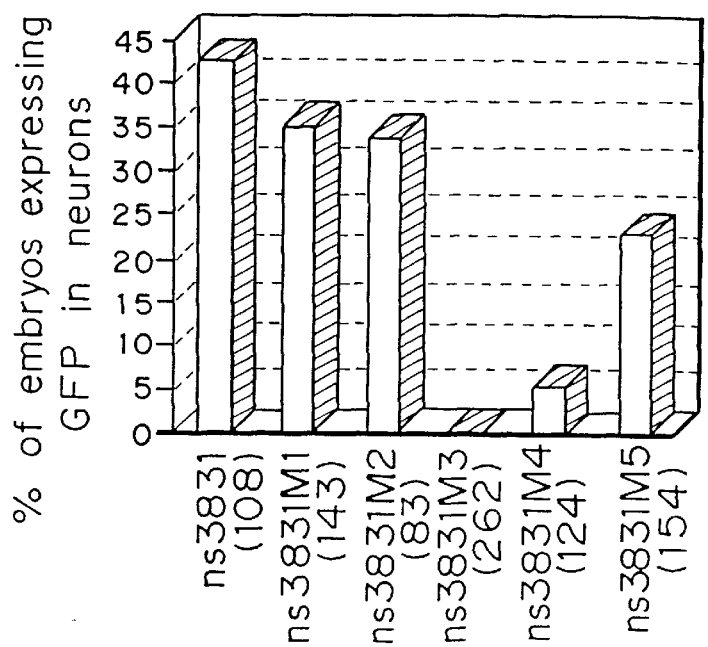
FIG. 7 is a graph of the percent of embryos microinjected with transgene constructs that expressed GFP in neurons. The transgene constructs were mutant forms of the ns3831 truncation of nsP5-GM2.

To determine the core sequence necessary for the activity of the neuron-specific element, five primers, each having two to three altered nucleotides within the 31 bp neuron-specific element (see above), were used to amplify nsP5-GM2. The PCR products obtained were directly injected into single cell embryos. This 31 bp sequence contains an Ets-like recognition site (AGGAC) in an inverted orientation which is present in several neuron-specific promoters (Chang and Thompson, J. Biol Chem 271:6467–75 (1996), Charron et al., J. Biol Chem 270:30604–10 (1995)). Therefore, four of the primers used in these PCR reactions contain altered nucleotides within the Ets-like recognition site or in the adjacent sequence. As expected, embryos injected with ns3831M1, which contains two mutant nucleotides that are thirteen nucleotides upstream of the Ets-like recognition site, showed little change in neuron-specific GFP expression (FIG. 7). A mutation of 2 nucleotides (ns3831M2) that lie three nucleotides upstream of the Ets-like recognition site had no effect on enhancer activity (FIG. 7). Mutation of two nucleotides just one nucleotide upstream of the Ets-like motif, contained in ns3831M3, completely eliminated the neuron-specific enhancer activity of the 31 bp element (FIG. 7). Mutation of three nucleotides (ns3831M4), of which two lie within the Ets-like recognition site, also resulted in a sharp decrease in enhancer activity (FIG. 7). A mutation of two nucleotides that lie within the Ets-like recognition site (ns3831 M5) reduced the neuron-specific enhancer activity of the 31 bp element by approximately 50% (FIG. 7). From this it was concluded that a CCCTCCT motif, which partially overlaps the Ets-like recognition site within the 31 bp sequence, is absolutely required for neuron-specific enhancer activity.

This dissection of expression sequences using transgenic fish, exemplified in zebrafish and with GATA-2 as described above, provides a system that allows the rapid and efficient identification of those cis-acting elements that play key roles in modulating the expression of developmentally regulated genes. Identification of these cis-acting elements is a useful step toward determining the genes that operate earlier than the gene under study in the specification of a developmental pathway (since the identified distal regulatory elements interact with transcription factors which must be expressed for the regulatory elements to function).

Careful analysis of GATA-2 promoter activity in zebrafish embryos revealed three distinct tissue specific enhancer elements. These three elements appear to act independently to enhance gene expression specifically in blood precursors, the EVL, or the CNS. Deletion of one or two of the elements will generate transgene constructs that can drive expression of a gene of interest in a specific tissue. Such constructs also allow study of the tissue-specific function of genes expressed in multiple tissues.

It has been shown that the developmental regulation of the mammalian HOX6 and GAP-43 promoter activities is conserved in zebrafish (Westerfield et al., *Genes Dev* 6:591–8 (1992), Reinhard et al., *Development* 120:1767–75 (1994)). If the same neuron-specific element identified in the zebrafish GATA-2 promoter is also shown to be required for neuron-specific activity of the mouse promoter, one could specifically knockout expression of GATA-2 in the mouse CNS by targeting this cis-element. This would allow one to determine precisely the role that GATA-2 plays in the CNS.

The neuron-specific enhancer element of GATA-2 has been precisely mapped and found to contain the core DNA consensus sequence for binding by Ets-related transcription factors. Although Ets-related factors have been implicated in the regulation of expression of a number of neuron-specific genes (Chang and Thompson, *J. Biol Chem* 271:6467–75 (1996), Charron et al., *J. Biol Chem* 270:30604–10 (1995)), another sequence, CCTCCT, present in this region of the zebrafish GATA-2 promoter was found to be required for expression in the CNS. This motif partially overlaps an inverted form of the core sequence of the Ets DNA binding recognition site. As has been shown for other genes, the activities of Ets family proteins often rely more on their ability to interact with other transcription factors than on specific binding to a cognate DNA sequence (Crepieux et al., *Crit Rev Oncog* 5:615–38 (1994)). It is possible that an independent factor that binds to the CCTCCT motif is required for neuron-specific activity of the GATA-2 promoter.

A number of growth factors are known to affect early embryonic expression of GATA-2. Noggin and activin, which both have dorsalizing activity in Xenopus embryos, downregulate GATA-2 expression in dorsal mesoderm (Walmsley et al., *Development* 120:2519–29 (1994)). BMP-4 activates GATA-2 expression in ventral mesoderm and is probably important to early blood progenitor proliferation (Maeno et al., *Blood* 88:1965–72 (1996)). Growth factors that might affect expression of GATA-2 in neurons are not known. However, both BMP-2 and BMP-6 can activate neuron-specific gene expression (Fann and Patterson, *J. Neurochem* 63:2074–9 (1994)). Consistent with studies on growth factors that upregulate or downregulate GATA-2 expression, GATA-2 promoter activity was excluded from the zebrafish dorsal shield. It has also been discovered that lithium chloride treatment dorsalizes the injected embryos and dramatically reduces GATA-2 promoter activity as determined by GFP expression.

Although GATA-2 expression has not been observed in the EVL by in situ hybridization on whole embryos, this may be due to the conditions used. In mouse, embryonic mast cells present in the skin have only been detected by in situ hybridization performed on skin tissue sections (Jippo et al., *Blood* 87:993–8 (1996)). Interestingly, expression of GATA-2 in mouse skin mast cells occurs only during a short period of embryogenesis, similar to what has been found for EVL cells in zebrafish. It is possible that the constructs used in this example may be missing elements that would specifically silence GATA-2 expression in the zebrafish EVL.

The method described above is generally applicable to the dissection of any developmentally regulated vertebrate promoter. Tissue specific and growth factor response elements can be rapidly identified in this manner. The fact that zebrafish typically produce hundreds of fertilized eggs per mating facilitates obtaining statistically significant results. While tissue culture systems have been useful for identifying many important transcription factors, transfection analysis in tissue culture cells cannot simulate the complex, rapidly changing microenvironment to which the promoter must respond during embryogenesis. Temporal and spatial analysis of promoter activity can be only poorly mimicked in vitro. The system described herein allows complete analysis of promoter activity in all tissues of a whole vertebrate.

I claim:

1. A transgenic zebrafish that expresses a heterologous expression product, comprising a zebrafish cell lineage-specific expression sequence operably linked to a sequence encoding a heterologous expression product, wherein the sequence encoding the expression product is integrated into the genome of the zebrafish and wherein expression of the heterologous expression product is cell lineage-specific.

2. The transgenic zebrafish of claim 1 wherein the expression product is a reporter protein.

3. The transgenic zebrafish of claim 2 wherein the reporter protein is selected from the group consisting of β-galactosidase, chloramphenicol acetyltransferase, and green fluorescent protein.

4. The transgenic zebrafish of claim 3 wherein the reporter protein is green fluorescent protein.

5. The transgenic zebrafish of claim 1 wherein the expression product is expressed only in cells selected from the group consisting of blood cells, nerve cells, and skin cells.

6. The transgenic zebrafish of claim 5 wherein the expression product is expressed only in blood cells.

7. The transgenic zebrafish of claim 6 wherein the expression product is expressed only in erythroid progenitor cells.

8. The transgenic zebrafish of claim 5 wherein the expression product is expressed only in neurons.

9. The transgenic zebrafish of claim 1 wherein expression of the expression product is stable and transmitted through the germline.

10. The transgenic zebrafish of claim 1, wherein the zebrafish expression sequence and the sequence encoding the expression product are contained in an exogenous construct.

11. The transgenic zebrafish of claim 10 wherein the expression sequence is selected from the group consisting of a GATA-1 expression sequence and a GATA-2 expression sequence.

12. The transgenic zebrafish of claim 11 wherein the expression sequence comprises a GATA-1 expression sequence.

13. The transgenic zebrafish of claim 11 wherein the expression sequence comprises a GATA-2 expression sequence.

14. The transgenic zebrafish of claim 13, wherein the expression sequence comprises the GATA-2 promoter operably linked to the neuron-specific enhancer of GATA-2.

15. The transgenic zebrafish of claim 13 wherein the expression sequence comprises the GATA-2 promoter operably linked to the blood-specific enhancer of GATA-2.

16. The transgenic zebrafish of claim 13 wherein the expression sequence comprises the GATA-2 promoter operably linked to the skin-specific enhancer of GATA-2.

17. The transgenic zebrafish of claim 10 wherein the construct further comprises (a) intron sequences operably linked to the sequence encoding the expression product, (b) a polyadenylation signal operably linked to the sequence encoding the expression product, or both.

18. The transgenic zebrafish of claim 1 wherein the expression sequence is a promoter.

19. The transgenic zebrafish of claim 1 wherein the transgenic zebrafish is developed from, or is the progeny of a transgenic zebrafish developed from, an embryonic cell into which the sequence encoding the heterologous expression product was introduced.

20. The transgenic zebrafish of claim 1 wherein the expression product is expressed in predetermined cell lineages.

21. The transgenic zebrafish of claim 1 wherein the sequence encoding the heterologous expression product is genetically linked to an identified mutant gene.

22. The transgenic zebrafish of claim 1 wherein the expression sequence comprises a zebrafish promoter operably linked to a zebrafish enhancer.

23. The transgenic zebrafish of claim 22 wherein the expression sequence further comprises zebrafish 5' untranslated sequences operably linked to the promoter and the sequence encoding the expression product.

24. Cells isolated from the transgenic zebrafish of claim 1 wherein the cells express the expression product.

25. A method of making transgenic zebrafish, the method comprising:

(a) introducing an exogenous construct into a zebrafish egg cell or embryonic cell, wherein the construct comprises a zebrafish cell lineage-specific expression sequence operably linked to a sequence encoding an expression product, and (b) allowing the egg cell or embryonic cell to develop into a zebrafish, wherein expression of the expression product in the zebrafish is cell lineage-specific, wherein the exogenous construct is integrated into the genome of the zebrafish.

26. The method of claim 25 wherein the expression product is expressed in predetermined cell lineages.

27. The method of claim 25 wherein the method further comprises producing progeny of the zebrafish.

28. The method of claim 25 wherein the expression sequence comprises a zebrafish promoter operably linked to a zebrafish enhancer.

29. A method of identifying a compound that affects cell lineage-specific expression, the method comprising exposing the zebrafish of claim 1 or progeny of the zebrafish to a test compound, detecting the expression product in the zebrafish exposed to the test compound, and comparing the pattern of expression of the expression product in the zebrafish exposed to the test compound with the pattern of expression of the expression product in the zebrafish of claim 1 or progeny of the zebrafish not exposed to the test compound, wherein if the pattern of expression of the expression product in the zebrafish exposed to the test compound differs from the pattern of expression in the zebrafish not expo ed to the test compound, then the test compound affects cell-lineage specific expression.

30. A method of identifying the pattern of expression of a zebrafish gene, the method comprising detecting the expression product in the zebrafish of claim 1 or progeny of the zebrafish, wherein the expression sequence is an expression sequence of a zebrafish gene, wherein the pattern of expression of the expression product in the zebrafish or progeny of the zebrafish identifies the pattern of expression of the zebrafish gene.

31. A method of identifying a mutant gene that affects expression of a zebrafish gene, the method comprising crossing the zebrafish of claim 10 or progeny of the zebrafish to a second zebrafish having an identified mutant gene to produce a third zebrafish having both the exogenous construct and the identified mutation, wherein the expression sequence is an expression sequence of a zebrafish gene, detecting the expression product in the third zebrafish or progeny of the third zebrafish, and comparing the pattern of expression of the expression product in the third zebrafish or the progeny of the third zebrafish with the pattern of expression of the expression product in the zebrafish, wherein if the pattern of expression of the expression product in the third zebrafish or progeny of the third zebrafish differs from the pattern of expression in the zebrafish, then the mutant gene affects expression of the zebrafish gene.

32. A method of marking a mutant gene, the method comprising crossing the zebrafish of claim 10 or progeny of the zebrafish to a second zebrafish having an identified mutant gene, wherein the exogenous construct and the mutant gene map to the same region of the genome, to produce a third zebrafish having both the exogenous construct and the mutant gene, and crossing the third zebrafish to a fourth zebrafish, wherein the fourth zebrafish has neither the exogenous construct nor the mutant gene, to produce a fifth zebrafish, wherein the fifth zebrafish has both the exogenous construct and the mutant gene, wherein the mutant gene is marked by the exogenous construct in the fifth zebrafish.

33. The method of claim 32, wherein the method further comprises crossing the fifth zebrafish, or a progeny of the fifth zebrafish, with a sixth zebrafish, and identifying progeny zebrafish expressing the expression product, wherein zebrafish expressing the expression product have the mutant gene.

34. A method of identifying genes, the method comprising:

isolating from the zebrafish of claim 1 or progeny thereof a cell expressing a cell-lineage specific expression product, and identifying genes that are expressed in the cell.

35. The method of claim 34, wherein the gene is identified by extracting RNA and performing differential display.

36. The method of claim 34, wherein the gene is identified by extracting RNA and performing subtractive hybridization.

37. A method for identifying genes involved in cell lineage specific expression comprising:

a. introducing a mutation into the zebrafish of claim 1 and b. detecting a change in the expression product in the fish containing the mutation, whereby a change in the expression product identifies a gene involved in cell lineage specific expression.

38. A method of identifying compounds that affect expression of genes comprising:

a) contacting a zebrafish of claim 1 wherein the expression product is a directly detectable reporter protein with a compound;

b) comparing the expression of the expression product in zebrafish contacted with the compound with zebrafish that were not contacted with the compound;

c) determining the effect of the compound on the expression product.

* * * * *